(12) United States Patent
Allen et al.

(10) Patent No.: US 9,006,144 B2
(45) Date of Patent: Apr. 14, 2015

(54) GLYPHOSATE FORMULATIONS BASED ON COMPOSITIONS DERIVED FROM NATURAL OIL METATHESIS

(75) Inventors: Dave R. Allen, Chicago, IL (US); Randal J. Bernhardt, Antioch, IL (US); Andrew D. Malec, Chicago, IL (US); Patrick Shane Wolfe, Palatine, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 13/880,017

(22) PCT Filed: Oct. 25, 2011

(86) PCT No.: PCT/US2011/057616
§ 371 (c)(1),
(2), (4) Date: May 15, 2013

(87) PCT Pub. No.: WO2012/061106
PCT Pub. Date: May 10, 2012

(65) Prior Publication Data
US 2013/0237421 A1 Sep. 12, 2013

Related U.S. Application Data

(60) Provisional application No. 61/406,556, filed on Oct. 25, 2010, provisional application No. 61/406,547, filed on Oct. 25, 2010, provisional application No. 61/406,570, filed on Oct. 25, 2010.

(51) Int. Cl.
| | | |
|---|---|---|
| A01N 57/18 | (2006.01) | |
| A01N 57/00 | (2006.01) | |
| A61K 31/66 | (2006.01) | |
| C11C 3/08 | (2006.01) | |
| C07C 69/533 | (2006.01) | |
| C07C 69/593 | (2006.01) | |
| C11D 1/28 | (2006.01) | |
| C11D 1/74 | (2006.01) | |
| B01F 17/00 | (2006.01) | |

(Continued)

(52) U.S. Cl.
CPC ............... *C11C 3/08* (2013.01); *C07C 69/533* (2013.01); *C07C 69/593* (2013.01); *C11D 1/28* (2013.01); *C11D 1/74* (2013.01); *B01F 17/0028* (2013.01); *B01F 17/0057* (2013.01); *C11D 1/83* (2013.01); *C11D 1/94* (2013.01); *C07C 211/21* (2013.01); *C07C 237/16* (2013.01); *A01N 25/04* (2013.01); *A01N 33/12* (2013.01); *A01N 37/18* (2013.01); *A01N 37/44* (2013.01); *A01N 41/04* (2013.01); *A61K 8/416* (2013.01); *A61K 8/42* (2013.01); *A61K 8/44* (2013.01); *A61K 8/466* (2013.01); *A61Q 5/12* (2013.01); *A61Q 19/10* (2013.01); *A62D 1/0071* (2013.01); *C09K 8/00* (2013.01); *C09K 15/28* (2013.01); *C11D 1/62* (2013.01); *C11D 1/90* (2013.01); *C11D 1/92* (2013.01); *C11D 1/04* (2013.01); *A01N 25/02* (2013.01); *A61K 8/92* (2013.01); *C08K 5/01* (2013.01); *C08K 5/20* (2013.01); *C11C 3/00* (2013.01); *C11D 3/48* (2013.01); *C07C 219/08* (2013.01); *A01N 25/30* (2013.01); *C07C 209/12* (2013.01); *C07C 231/12* (2013.01); *C07C 303/18* (2013.01); *C11D 1/002* (2013.01); *C11D 1/652* (2013.01); *C08G 65/2615* (2013.01)

(58) Field of Classification Search
None
See application file for complete search history.

(56) References Cited

U.S. PATENT DOCUMENTS

| 2,653,970 A | 9/1953 | Fessler et al. |
|---|---|---|
| 3,169,142 A | 2/1965 | Knaggs et al. |

(Continued)

FOREIGN PATENT DOCUMENTS

| WO | 0108480 | 2/2001 |
|---|---|---|
| WO | 0108482 | 2/2001 |

(Continued)

OTHER PUBLICATIONS

Tetrahedron 68 2012, 1117 , Yun et al.

(Continued)

*Primary Examiner* — Alton Pryor
(74) *Attorney, Agent, or Firm* — Dilworth IP LLC

(57) ABSTRACT

Aqueous glyphosate formulations comprising a surfactant derived from metathesized natural oil feedstocks are disclosed. The formulations comprise a glyphosate salt, water, and a surfactant derived from a metathesis-derived $C_{10}$-$C_{17}$ monounsaturated acid, octadecene-1,18-dioic acid, or their ester derivatives. The surfactant is selected from $C_{10}$ or $C_{12}$ amine oxides, $C_{10}$ or $C_{12}$ quats, $C_{10}$, $C_{12}$, or $C_{16}$ amidoamines, $C_{10}$ or $C_{12}$ amidoamine oxides, $C_{10}$ imidazoline quats, $C_{10}$ or $C_{12}$ amidoamine quats, $C_{10}$, $C_{12}$, or $C_{16}$ betaines, $C_{16}$ amidoamine betaines, $C_{18}$ diamidoamines, $C_{18}$ diamidoamine oxides, $C_{18}$ diamidoamine diquats, $C_{18}$ diamidoamine oxide quats, $C_{18}$ diamidoamine oxide betaines, Cis diamidoamine monobetaines, $C_{18}$ diamidoamine monobetaine quats, $C_{18}$ ester amidoamine quats, and amidoamines and their oxidized or quaternized derivatives made from self- or cross-metathesized palm or soybean oil. The surfactants noted above impart substantial stability to highly concentrated glyphosate formulations at, above, and below room temperature and perform as well or better than commercial alternatives.

16 Claims, No Drawings

(51) Int. Cl.

| | | |
|---|---|---|
| C11D 1/83 | (2006.01) | |
| C11D 1/94 | (2006.01) | |
| C07C 211/21 | (2006.01) | |
| C07C 237/16 | (2006.01) | |
| A01N 25/04 | (2006.01) | |
| A01N 33/12 | (2006.01) | |
| A01N 37/18 | (2006.01) | |
| A01N 37/44 | (2006.01) | |
| A01N 41/04 | (2006.01) | |
| A61K 8/41 | (2006.01) | |
| A61K 8/42 | (2006.01) | |
| A61K 8/44 | (2006.01) | |
| A61K 8/46 | (2006.01) | |
| A61Q 5/12 | (2006.01) | |
| A61Q 19/10 | (2006.01) | |
| A62D 1/02 | (2006.01) | |
| C09K 8/00 | (2006.01) | |
| C09K 15/28 | (2006.01) | |
| C11D 1/62 | (2006.01) | |
| C11D 1/90 | (2006.01) | |
| C11D 1/92 | (2006.01) | |
| C11D 1/04 | (2006.01) | |
| A01N 25/02 | (2006.01) | |
| A61K 8/92 | (2006.01) | |
| C08K 5/01 | (2006.01) | |
| C08K 5/20 | (2006.01) | |
| C11C 3/00 | (2006.01) | |
| C11D 3/48 | (2006.01) | |
| C07C 219/08 | (2006.01) | |
| A01N 25/30 | (2006.01) | |
| C07C 209/12 | (2006.01) | |
| C07C 231/12 | (2006.01) | |
| C07C 303/18 | (2006.01) | |
| C11D 1/00 | (2006.01) | |
| C11D 1/65 | (2006.01) | |
| C08G 65/26 | (2006.01) | |

(56) References Cited

U.S. PATENT DOCUMENTS

| | | | |
|---|---|---|---|
| 3,544,613 A | 12/1970 | Knaggs et al. | |
| 4,087,457 A | 5/1978 | Convers et al. | |
| 4,140,513 A | 2/1979 | Prill | |
| 4,148,821 A | 4/1979 | Nussbaum et al. | |
| 4,275,013 A | 6/1981 | Tokosh et al. | |
| 4,405,531 A | 9/1983 | Franz | |
| 4,545,941 A | 10/1985 | Rosenburg | |
| 4,965,403 A | 10/1990 | Fields, Jr. et al. | |
| 5,226,943 A | 7/1993 | Hulshof | |
| 5,482,908 A | 1/1996 | Le-khac | |
| 5,538,937 A | 7/1996 | Hasebe et al. | |
| 5,700,760 A | 12/1997 | Magin et al. | |
| 5,703,016 A | 12/1997 | Magin et al. | |
| 5,710,103 A | 1/1998 | Magin et al. | |
| 5,728,649 A | 3/1998 | Hasebe et al. | |
| 5,750,468 A | 5/1998 | Wright et al. | |
| 5,849,663 A | 12/1998 | Hasebe et al. | |
| 5,858,921 A | 1/1999 | Magin et al. | |
| 5,958,439 A | 9/1999 | Gubelmann et al. | |
| 5,985,794 A | 11/1999 | Hasebe et al. | |
| 6,130,186 A | 10/2000 | Ward et al. | |
| 6,277,788 B1 | 8/2001 | Wright | |
| 6,451,735 B1 | 9/2002 | Ottaway et al. | |
| 6,455,473 B2 | 9/2002 | Wright | |
| 6,475,953 B1 | 11/2002 | Ward et al. | |
| 6,645,912 B1 | 11/2003 | Mille et al. | |
| 6,653,257 B2 | 11/2003 | Mille et al. | |
| 6,747,164 B2 | 6/2004 | Gustavsson et al. | |
| 6,897,184 B2 | 5/2005 | Kurita et al. | |
| 6,908,882 B1 | 6/2005 | Becher et al. | |
| 6,992,046 B2 | 1/2006 | Bramati et al. | |
| 7,049,270 B2 | 5/2006 | Lennon et al. | |
| 7,135,437 B2 | 11/2006 | Pallas et al. | |
| 7,316,990 B2 | 1/2008 | Tank | |
| 7,576,227 B2 | 8/2009 | Bicerano et al. | |
| 7,960,599 B2 | 6/2011 | Millis et al. | |
| 8,034,979 B2 | 10/2011 | Zhu et al. | |
| 8,067,610 B2 | 11/2011 | Schrodi | |
| 2003/0087764 A1 | 5/2003 | Pallas et al. | |
| 2003/0158042 A1 | 8/2003 | Bramati et al. | |
| 2005/0170965 A1 | 8/2005 | Bramati et al. | |
| 2007/0118916 A1 | 5/2007 | Puzio et al. | |
| 2008/0033026 A1 | 2/2008 | Zullo et al. | |
| 2008/0103047 A1 | 5/2008 | Gioia et al. | |
| 2008/0312083 A1 | 12/2008 | Gioia | |
| 2009/0018018 A1 | 1/2009 | Gioia et al. | |
| 2009/0048459 A1 | 2/2009 | Tupy et al. | |
| 2009/0181850 A1 | 7/2009 | Ferguson et al. | |
| 2009/0264672 A1 | 10/2009 | Abraham et al. | |
| 2009/0318294 A1 | 12/2009 | Malec et al. | |
| 2010/0113274 A1* | 5/2010 | Hemminghaus et al. | 504/206 |
| 2010/0145086 A1 | 6/2010 | Schrodi et al. | |
| 2010/0234228 A1 | 9/2010 | Lennon et al. | |
| 2010/0279869 A1 | 11/2010 | Bramati et al. | |
| 2010/0282467 A1 | 11/2010 | Hutchison et al. | |
| 2010/0331182 A1 | 12/2010 | Zhang et al. | |
| 2011/0113679 A1 | 5/2011 | Cohen et al. | |
| 2011/0210028 A1 | 9/2011 | Zhu | |
| 2011/0313180 A1* | 12/2011 | Uptain et al. | 554/124 |
| 2012/0071676 A1 | 3/2012 | Schrodi et al. | |
| 2012/0157313 A1 | 6/2012 | Zhu et al. | |
| 2012/0197031 A1 | 8/2012 | Firth et al. | |
| 2013/0035502 A1 | 2/2013 | Cohen et al. | |
| 2013/0035532 A1 | 2/2013 | Schrodi | |

FOREIGN PATENT DOCUMENTS

| | | |
|---|---|---|
| WO | 0132019 | 5/2001 |
| WO | 0195720 | 12/2001 |
| WO | 2007143788 | 12/2007 |
| WO | WO-2008048522 | 4/2008 |
| WO | 2008068214 | 6/2008 |
| WO | 2010036996 | 4/2010 |
| WO | 2011057361 | 5/2011 |

OTHER PUBLICATIONS

Appl. Catal. A. 346 2009, 158, Djigoue et al.
J.C. Mol., Topics in Catalysis 27 2004, 97.
J. C. Mol., Green Chem., 4 2002, 5.
Org. Synth., vol. Coll. IV (1963), 635, unauthored.

* cited by examiner

GLYPHOSATE FORMULATIONS BASED ON COMPOSITIONS DERIVED FROM NATURAL OIL METATHESIS

FIELD OF THE INVENTION

The invention relates to glyphosate formulations, and particularly to compositions useful therein that derive from natural oil metathesis.

BACKGROUND OF THE INVENTION

N-Phosphonomethylglycine ("glyphosate") is a well-known, post-emergent, foliar-applied herbicide. When glyphosate formulations are applied to green leaves or stems, glyphosate moves through the plant so the entire plant dies. Glyphosate works by disrupting a plant enzyme, EPSP synthase, involved in the production of amino acids that are essential to plant growth. Because the enzyme is not present in humans or animals, glyphosate has very low toxicity to humans or animals. Glyphosate is typically formulated and applied in the form of a water-soluble agriculturally acceptable salt, e.g., the potassium or isopropylamine salt.

Surfactants are employed as adjuvants in glyphosate salt formulations to enhance herbicidal effectiveness. Surfactants help the formulations perform by improving two aspects of a spray droplet: wetting of the leaf surface and penentration of the spray droplet through the leaf cuticle into the plant tissues. Adjuvants further aid in the systemic translocation of the herbicide throughout the plant. A wide variety of surfactants have been taught as suitable for use (see, for example, the exhaustive lists of surfactant types taught in U.S. Pat. Nos. 7,049,270 and 7,135,437). A continuing issue with glyphosate formulations is how to formulate highly concentrated aqueous glyphosate compositions while maintaining good stability, particularly at cold or elevated temperatures (see, e.g., U.S. Pat. Appl. Publ. No. 2009/0318294).

Glyphosate formulations have been prepared containing surfactants such as fatty amine oxides, amidoamines, alkylbetaines, and other compositions (see, e.g., U.S. Pat. Nos. 6,908,882 and 6,992,046 and U.S. Pat. Appl. Publ. Nos. 2010/0113274 and 2009/0018018). These surfactants are made by derivatizing fatty esters or amides made from triglycerides, typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The fatty ester is a good starting material for making the amine oxide, amidoamine, or alkylbetaine.

Recent improvements in metathesis catalysts (see J. C. Mol, *Green Chem.* 4 (2002) 5) provide an opportunity to generate reduced chain length, monounsaturated to feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. As Professor Mol explains, metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, surfactants have generally not been made from these feedstocks.

We recently described new compositions made from feedstocks based on self-metathesis of natural oils or cross-metathesis of natural oils and olefins. In particular, we identified esteramines and ester quats, fatty amides, fatty amines and amidoamines, quaternized amines, betaines, sulfobetaines, alkoxylates, sulfonates, sulfo-estolides, and other compositions made by derivatizing the unique feedstocks (see application Ser. Nos. 13/878,550, 13/878,556, 13/878,972, 13/878,981, 13/879,786, and 13/880,007, respectively), all filed Oct. 25, 2011. The feedstocks, which include metathesis-derived $C_{10}$-$C_{17}$ monounsaturated acids, octadecene-1,18-dioic acid, and their ester derivatives, preferably have at least 1 mole % of trans-$\Delta^9$ unsaturation. Because the ability of a particular surfactant or blend of surfactants to impart stability to a glyphosate formulation over a wide temperature range is not easily inferred from surfactant structure, we performed extensive experimental investigations to identify subclasses of surfactants having these benefits.

New surfactant classes are always of interest to formulators of glyphosate formulations. Surfactants based on renewable resources will continue to be in demand as alternatives to petroleum-based surfactants. Traditional natural sources of fatty acids and esters used for making surfactants generally have predominantly (or exclusively) cis-isomers and lack relatively short-chain (e.g., $C_{10}$ or $C_{12}$) unsaturated Zs fatty portions. Metathesis chemistry provides an opportunity to generate precursors having shorter chains and mostly trans-isomers, which could impart improved performance when the precursors are converted to downstream compositions (e.g., in surfactants). Formulators will benefit from identification of particular subclasses of surfactants that derive from renewable sources and have desirable attributes for glyphosate formulations.

SUMMARY OF THE INVENTION

The invention relates to aqueous glyphosate formulations. The formulations comprise a glyphosate salt, water, and a surfactant derived from a metathesis-derived $C_{10}$-$C_{17}$ monounsaturated acid, octadecene-1,18-dioic acid, or their ester derivatives. The surfactant is selected from $C_{10}$ or $C_{12}$ amine oxides, $C_{10}$ or $C_{12}$ quats, $C_{10}$, $C_{12}$, or $C_{16}$ amidoamines, $C_{10}$ or $C_{12}$ amidoamine oxides, $C_{10}$ imidazoline quats, $C_{10}$ or $C_{12}$ amidoamine quats, $C_{10}$, $C_{12}$, or $C_{16}$ betaines, $C_{16}$ amidoamine betaines, $C_{18}$ diamidoamines, $C_{18}$ diamidoamine oxides, $C_{18}$ diamidoamine diquats, $C_{18}$ diamidoamine oxide quats, $C_{18}$ diamidoamine oxide betaines, $C_{18}$ diamidoamine monobetaines, $C_{18}$ diamidoamine monobetaine quats, $C_{18}$ ester amidoamine quats, and amidoamines and their oxidized or quaternized derivatives made from self- or cross-metathesized palm or soybean oil.

We surprisingly found that the surfactants noted above impart substantial stability to highly concentrated glyphosate formulations at, above, and below room temperature and perform as well or better than commercial alternatives.

DETAILED DESCRIPTION OF THE INVENTION

Aqueous glyphosate formulations of the invention comprise a glyphosate salt, water, and a surfactant derived from natural oil metathesis.

The glyphosate salts are normally made by neutralizing commercially supplied glyphosate acid in aqueous solution. Glyphosate acid is commercially available and can come from any desired source. One common commercial material is supplied at about 90.5% glyphosate acid. A basic compound (e.g., an alkali metal hydroxide or an amine) is ordinarily added with appropriate cooling to the aqueous glyphosate acid slurry with good mixing to generate the glyphosate concentrate. Suitable glyphosate salts include alkali metal salts (lithium, sodium, potassium), ammonium salts, salts of alkylamines (methylamine, ethylamine, isopropylamine salts), salts of alkanolamines (ethanolamine, dimethylethanolamine), and the like. For additional examples, see U.S. Pat. Nos. 7,316,990; 7,049,270; 6,277,788; 4,965,403; 4,405,531; and 4,140,513, the teachings of which are incorporated herein by reference.

An advantage of the inventive compositions is their stability over a wide temperature range at even high concentrations. Thus, the glyphosate formulations preferably comprise at least 30 wt. % acid equivalents, more preferably at least 36 wt. % acid equivalents, and most preferably at least 39 wt. % acid equivalents, of the glyphosate salt. Preferably, the glyphosate salt comprises an alkali metal, more preferably sodium or potassium, and most preferably potassium. For potassium glyphosate, 39 wt. % acid equivalents (or 39 wt. % "a.e.") corresponds to about 48 wt. % of the potassium salt because the potassium salt has a higher molecular weight than the acid by a factor of about 1.23. Thus, it takes about 23% by weight more of the potassium salt to deliver the same amount of glyphosate acid as would be provided by the pure acid. The solubility of glyphosate acid in water is low, about 2% by weight maximum (see references already cited above). Other advantages of using the aqueous salt of glyphosate are ease of transportation, handling, and end use of the product.

The amount of water used is typically in the range of 5 to 50 wt. %, preferably from 15 to 40 wt. %, and more preferably from 25 to 35 wt. %. Conveniently, the glyphosate formulation is supplied or sold as a concentrate and contains the minimum amount of water needed to dissolve the components. The ultimate customer may dilute the concentrate with water for normal use.

A surfactant derived from metathesis of a natural oil is included. However, not all such compositions are suitable for use. Through extensive experimentation, we identified particular classes of surfactants that provide glyphosate formulations with better stability over a wide temperature range compared with commercial alternatives.

Thus, suitable surfactants derive from a metathesis-derived $C_{10}$-$C_{17}$ monounsaturated acid, octadecene-1,18-dioic acid, or their ester derivatives and are selected from $C_{10}$ or $C_{12}$ amine oxides, $C_{10}$ or $C_{12}$ quats, $C_{10}$, $C_{12}$, or $C_{16}$ amidoamines, $C_{10}$ or $C_{12}$ amidoamine oxides, $C_{10}$ imidazoline quats, $C_{10}$ or $C_{12}$ amidoamine quats, $C_{10}$, $C_{12}$, or $C_{16}$ betaines, $C_{16}$ amidoamine betaines, $C_{18}$ diamidoamines, $C_{18}$ diamidoamine oxides, $C_{18}$ diamidoamine diquats, $C_{18}$ diamidoamine oxide quats, $C_{18}$ diamidoamine oxide betaines, $C_{18}$ diamidoamine monobetaines, $C_{18}$ diamidoamine monobetaine quats, $C_{18}$ ester amidoamine quats, and amidoamines and their oxidized or quaternized derivatives made from self- or cross-metathesized palm or soybean oil.

The amount of surfactant used is typically within the range of 0.1 to 15 wt. %, preferably from 1 to 10 wt. %, and more preferably from 2 to 5 wt. %.

As the examples below demonstrate, the inventive glyphosate formulations have good stability at, above, and below room temperature. We found that only certain subclasses of tested compositions perform as well or better than the control, while other compositions, often structurally similar, perform poorly in the test (see Table 5).

The $C_{10}$-$C_{17}$ monounsaturated acid, octadecene-1,18-dioic acid, or their ester derivatives used as a reactant is derived from metathesis of a natural oil. Traditionally, these materials, particularly the short-chain acids and derivatives (e.g., 9-decylenic acid or 9-dodecylenic acid) have been difficult to obtain except in lab-scale quantities at considerable expense. However, because of the recent improvements in metathesis catalysts, these acids and their ester derivatives are now available in bulk at reasonable cost. Thus, the $C_{10}$-$C_{17}$ monounsaturated acids and esters are conveniently generated by cross-metathesis of natural oils with olefins, preferably α-olefins, and particularly ethylene, propylene, 1-butene, 1-hexene, 1-octene, and the like. Self-metathesis of the natural oil or a $C_{10}$ acid or ester precursor (e.g., methyl 9-decenoate) provides the $C_{18}$ diacid or diester in optimal yield when it is the desired product.

Preferably, at least a portion of the $C_{10}$-$C_{17}$ monounsaturated acid has "$\Delta^9$" unsaturation, i.e., the carbon-carbon double bond in the $C_{10}$-$C_{17}$ acid is at the 9-position with respect to the acid carbonyl. In other words, there are preferably seven carbons between the acid carbonyl group and the olefin group at C9 and C10. For the $C_{11}$ to $C_{17}$ acids, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty acids that have $\Delta^9$ unsaturation, e.g., oleic acid, usually have ~100% cis-isomers.

Although a high proportion of trans-geometry (particularly trans-$\Delta^9$ geometry) may be desirable in the metathesis-derived fatty amines and derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal. A: General* 346 (2009) 158, especially FIG. 3. Thus, the skilled person might modify the reaction conditions to control the degree of isomerization or alter the proportion of cis- and trans-isomers generated.

For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated acid or ester) imparts different physical properties to surfactant compositions made from them, including, for example, modified physical form, melting range, compactability, and other important properties. These differences should allow formulators that use surfactants greater latitude or expanded choice as they use them in cleaners, fabric treatment, personal care, hard surface cleaners, and other end uses, particularly agricultural uses such as formulating storage-stable, highly concentrated glyphosate formulations. We sometimes noted advantages of selecting certain 100% trans-$C_{18}$ compositions, even when compared with their very similar 80:20 trans-/cis-analogs (see Table 5, C18-26 versus Mix-26). However, other 80:20 trans-/cis-compositions performed as well as their all-trans counterparts (see C18-29 versus Mix-29).

Suitable metathesis-derived $C_{10}$-$C_{17}$ monounsaturated acids include, for example, 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like, and their ester derivatives.

Usually, cross-metathesis or self-metathesis of the natural oil is followed by separation of an olefin stream from a modified oil stream, typically by distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is self-metathesized, the alkyl ester mixture will include a $C_{18}$ unsaturated diester. When the natural oil is cross-metathesized with an α-olefin, the alkyl ester mixture includes a $C_{10}$ unsaturated alkyl ester and one or more $C_{11}$ to $C_{17}$ unsaturated alkyl ester coproducts. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. As is demonstrated in the examples below, the $C_{10}$ unsaturated alkyl ester is readily separated from the $C_{11}$ to $C_{17}$ unsaturated alkyl ester and each is easily purified by fractional distillation. These alkyl esters are excellent starting materials for making surfactants for the inventive glyphosate formulations.

Natural oils suitable for use as a feedstock to generate the $C_{10}$-$C_{17}$ monounsaturated acid, octadecene-1,18-dioic acid, or their ester derivatives from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, tallow, lard, poultry fat, fish oil, and the like. Soybean oil, palm oil, rapeseed oil, and mixtures thereof are preferred natural oils.

Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty acid residues derived from oleic acid. Thus, particularly preferred natural oils include soybean oil, palm oil, algal oil, and rapeseed oil.

A modified natural oil, such as a partially hydrogenated vegetable oil, can be used instead of or in combination with the natural oil. When a natural oil is partially hydrogenated, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to surfactant compositions for the glyphosate formulations.

An alternative to using a natural oil as a feedstock to generate the $C_{10}$-$C_{17}$ monounsaturated acid, octadecene-1, 18-dioic acid, or their ester derivatives from self-metathesis or cross-metathesis with olefins is a monounsaturated fatty acid obtained by the hydrolysis of a vegetable oil or animal fat, or an ester or salt of such an acid obtained by esterification of a fatty acid or carboxylate salt, or by transesterification of a natural oil with an alcohol. Also useful as starting compositions are polyunsaturated fatty esters, acids, and carboxylate salts. The salts can include an alkali metal (e.g., Li, Na, or K); an alkaline earth metal (e.g., Mg or Ca); a Group 13-15 metal (e.g., B, Al, Sn, Pb, or Sb), or a transition, lanthanide, or actinide metal. Additional suitable starting compositions are described at pp. 7-17 of PCT application WO 2008/048522, the contents of which are incorporated by reference herein.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

$$M[X^1X^2L^1L^2(L^3)_n]=C_m=C(R^1)R^2$$

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. to Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

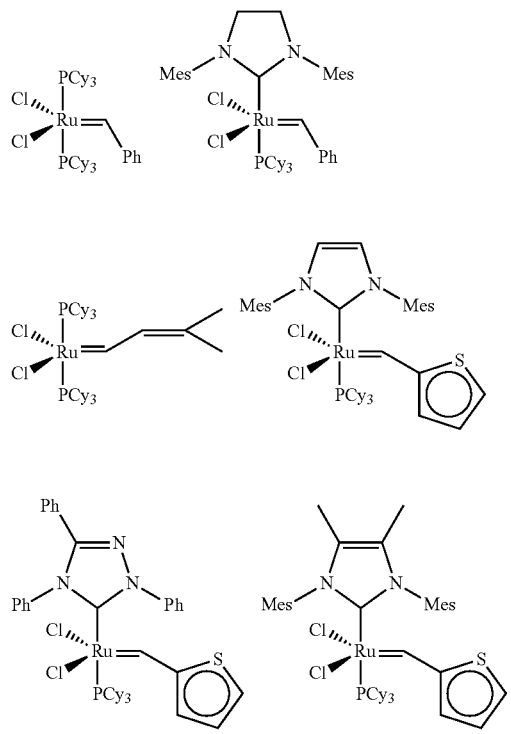

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein.

The $C_{10}$-$C_{17}$ monounsaturated acid, octadecene-1,18-dioic acid, or their ester derivatives used to make the surfactant come from natural oil metathesis as is detailed fully above. The feedstocks are converted to particular subclasses of amine oxides, amidoamines, amidoamine oxides, quaternized imidazolines, quaternized amidoamines, betaines, and other compositions that are useful as surfactants in glyphosate formulations. General synthetic procedures for making these compositions are provided below (General procedures B-K) and are summarized for each particular composition prepared in Table 2. For instance, amine oxide C10-39 is conveniently made using Methods E, G, and D by reacting methyl 9-dodecenoate with DMA to make the amide, followed by reduction of the amide to an amine with lithium aluminum hydride, followed by oxidation of the amine with hydrogen peroxide to give the amine oxide.

In a preferred aspect, the surfactant is selected from $C_{12}$ amine oxides, $C_{10}$ amidoamines, $C_{10}$ or $C_{12}$ amidoamine oxides, $C_{18}$ diamidoamines, $C_{18}$ diamidoamine oxides, $C_{18}$ diamidoamine monobetaines, $C_{18}$ diamidoamine oxide betaines, $C_{18}$ diamidoamine oxide quats, $C_{18}$ ester amidoamine quats, amidoamines and their oxidized or quaternized derivatives made from self-metathesized palm or soybean oil, and amidoamines and their oxidized or quaternized derivatives made from cross-metathesized palm or soybean oil. As shown in Table 5A, compositions from these classes of surfactants demonstrated superior ability to stabilize highly concentrated glyphosate formulations at room temperature, −10° C., and 54° C.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. (The "C18-" series of products in the examples below, for instance, are nominally 100% trans-isomers whereas the "Mix-" series are nominally 80:20 trans-/cis-isomer mixtures.) Structures shown often refer to a principal product that may be accompanied by a lesser proportion of other components or positional isomers. For instance, reaction products from modified triglycerides are complex mixtures. As another example, sulfonation or sulfitation processes often give mixtures of sultones, alkanesulfonates, and alkenesulfonates, in addition to isomerized products. Thus, the structures provided represent likely or predominant products. Charges may or may not be shown but are understood, as in the case of amine oxide structures. Counterions, as in quaternized compositions, are not usually included, but they are understood by the skilled person from the context.

Particularly preferred surfactants are the $C_{12}$ amine oxides, $C_{10}$ amidoamines, and $C_{10}$ or $C_{12}$ amidoamine oxides. Exemplary compositions of this type:

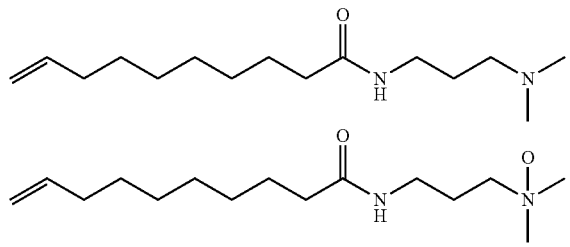

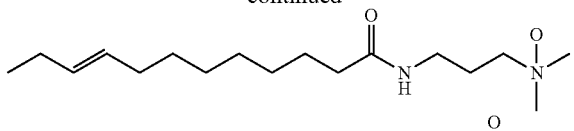

Particularly preferred surfactants include $C_{18}$ diamidoamines, $C_{18}$ diamidoamine oxides, $C_{18}$ diamidoamine monobetaines, $C_{18}$ diamidoamine oxide betaines, $C_{18}$ diamidoamine oxide quats, and $C_{18}$ ester amidoamine quats. A few examples:

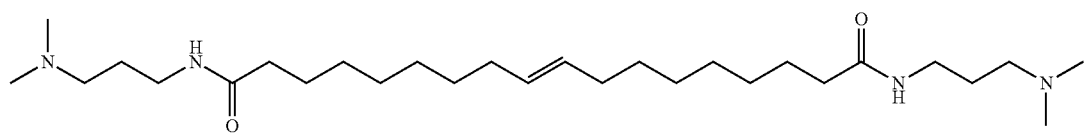

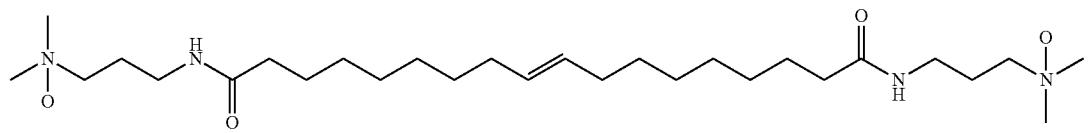

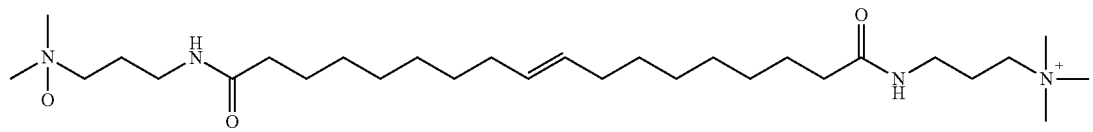

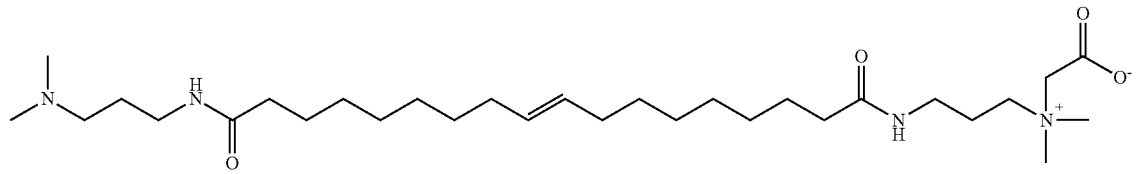

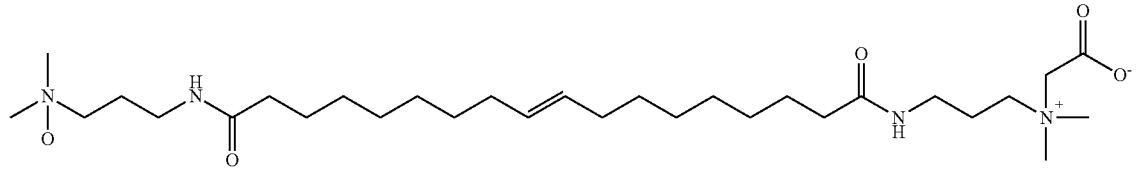

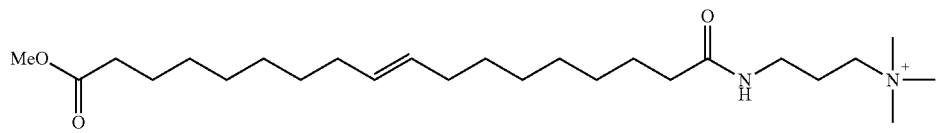

Particularly preferred surfactants also include amidoamines and their oxidized derivatives made from self-metathesized palm or soybean oil. One example of this type of complex mixture is "MTG-12," the amidoamine dioxide made by reacting self-metathesized soybean oil with DMAPA, followed by oxidation with hydrogen peroxide:

metathesized palm or soybean oil, and amidoamines and their oxidized or quaternized derivatives made from cross-metathesized palm or soybean oil.

As shown in Table 5A, compositions from these classes of surfactants demonstrate good ability to stabilize highly con-

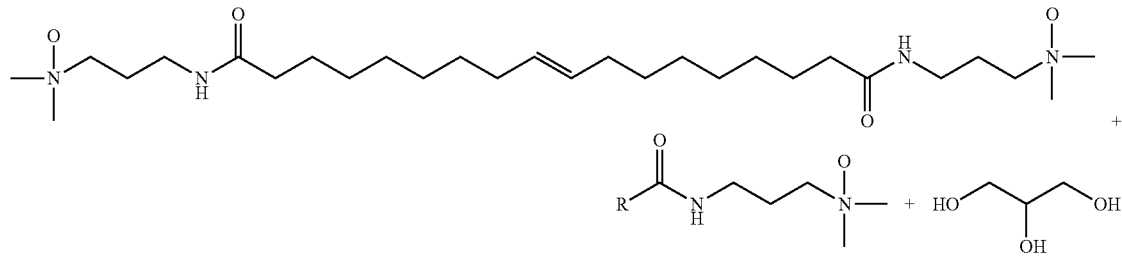

R = C16, C18 Sat. + Unsat.

Another example is "PMTG-5," an amidoamine made by reacting self-metathesized palm oil with DMAPA:

centrated glyphosate formulations at room temperature, −10° C., and 54° C.

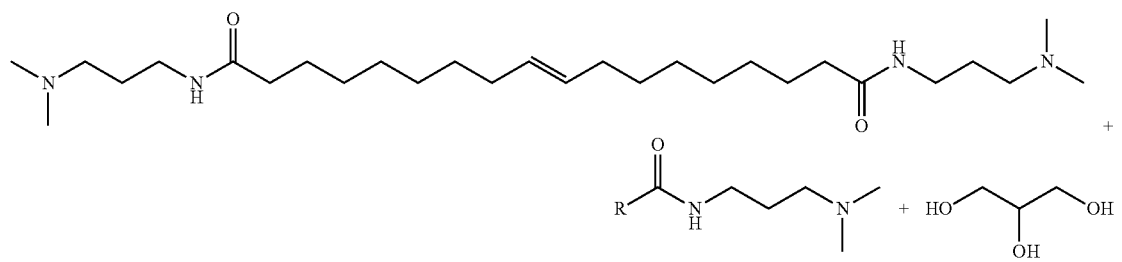

R = C16, C18 Sat. + Unsat.

In another aspect, the surfactant is selected from $C_{10}$ amine oxides, $C_{10}$ or $C_{12}$ quats, $C_{12}$ or $C_{16}$ amidoamines, $C_{10}$ imidazoline quats, $C_{10}$ or $C_{12}$ amidoamine quats, $C_{10}$, $C_{12}$, or $C_{16}$ betaines, $C_{16}$ amidoamine betaines, $C_{18}$ diamidoamine diquats, $C_{18}$ diamidoamine monobetaine quats, amidoamines and their oxidized or quaternized derivatives made from self- Preferred surfactants include the $C_{10}$ amine oxides, $C_{10}$ or $C_{12}$ quats, $C_{12}$ or $C_{16}$ amidoamines, $C_{10}$ imidazoline quats, $C_{10}$ or $C_{12}$ amidoamine quats, $C_{10}$, $C_{12}$, or $C_{16}$ betaines, and $C_{16}$ amidoamine betaines. Exemplary compositions of this type:

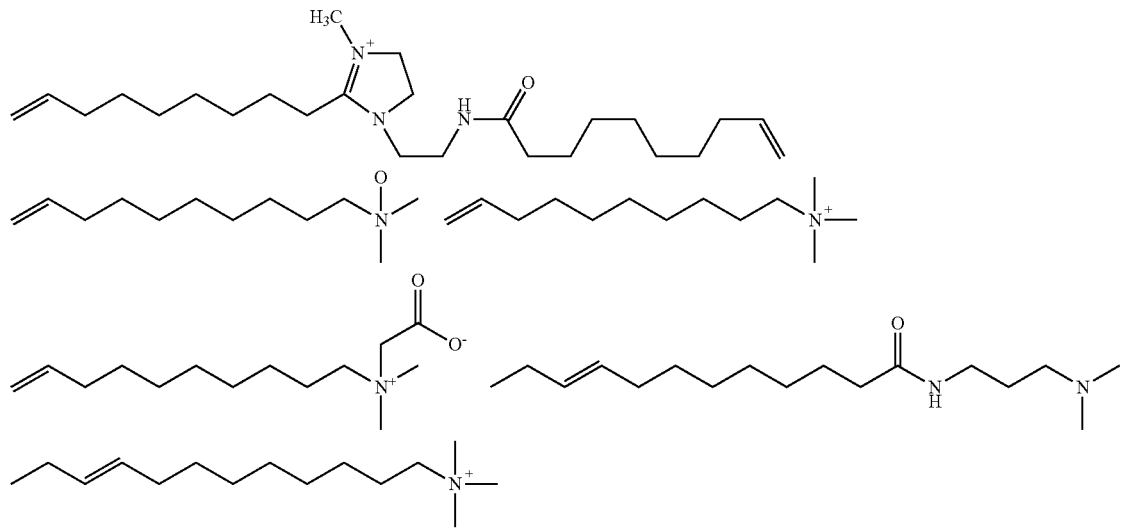

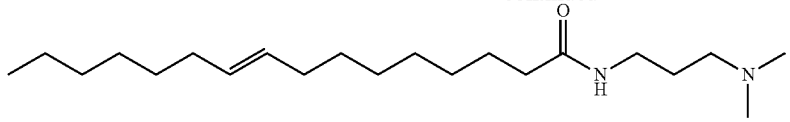
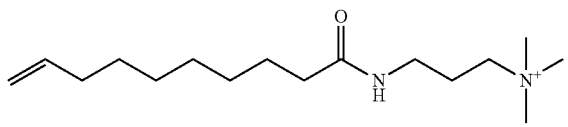
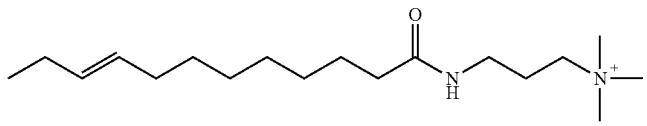
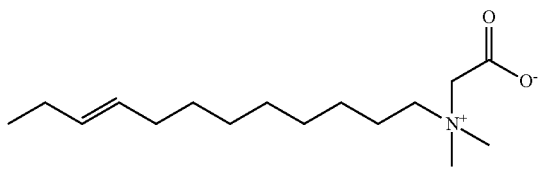
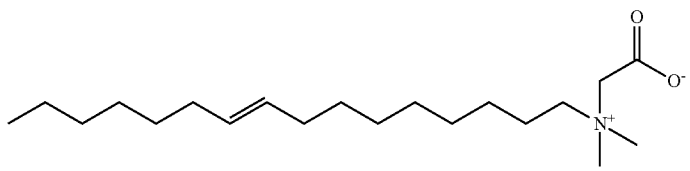
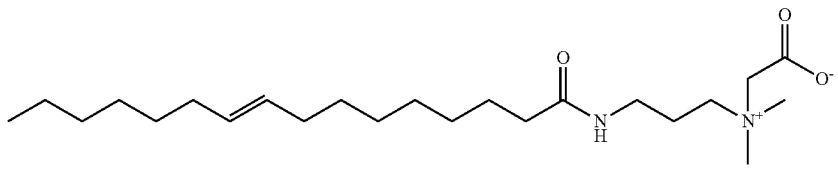
Preferred surfactants include C$_{18}$ diamidoamine diquats and C$_{18}$ diamidoamine monobetaine quats. Examples:
Preferred surfactants also include amidoamines and their oxidized or quaternized derivatives made from self-metathe-
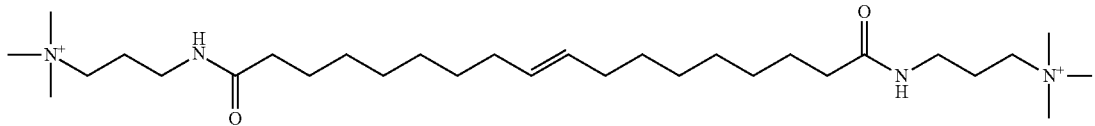
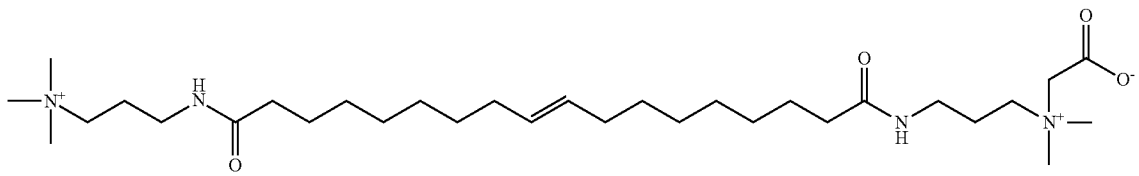

sized palm or soybean oil, and amidoamines and their oxidized or quaternized derivatives made from cross-metathesized palm or soybean oil.

One example of this type of complex mixture is "UTG-6," the amidoamine betaine made by reacting cross-metathesized (with 1-butene) soybean oil with DMAPA, followed by conversion to the betaine with sodium monochloroacetate:

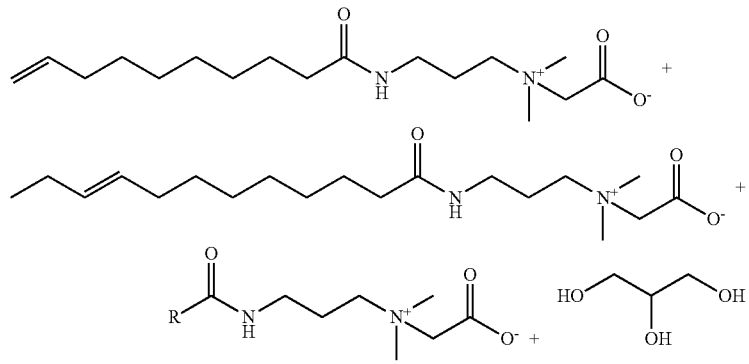

R = C16, C18 Sat.

The glyphosate formulation can include additional conventional components or adjuvants that do not detract from formulation stability or herbicidal activity. Commonly, the formulations might include a solvent, one or more auxiliary surfactants, herbicides, pesticides, or other agricultural actives, buffers, coupling agents, chelating agents, compatibilizers, corrosion inhibitors, dyes, odorants, penetration aids, wetting agents, spreading agents, dispersants, thickeners, antimicrobial agents, freezing point depressants, or the like.

Among auxiliary surfactants, anionic, cationic (e.g., quaternary ammonium surfactants), nonionic, amphoteric, or zwitterionic surfactants might be included. Preferably, the auxiliary surfactant is a nonionic or amphoteric surfactant. Suitable nonionic surfactants include, for example, fatty alcohols, alcohol fatty esters, fatty alcohol ethoxylates, ethoxylated alkylphenols, ethoxylated castor oils, ethoxylated fatty acids, ethoxylated fatty amines, fatty amides, amidoamines, tallow amine ethoxylates, alkylpolyglucosides, glycerol esters, and the like. Suitable amphoteric surfactants include, for example, fatty amine oxides, betaines, sulfobetaines, and the like. Other suitable nonionic and amphoteric surfactants are disclosed in U.S. Pat. Nos. 7,049,270 and 7,135,437, and U.S. Pat. Appl. Publ. No. 2010/0331182, the teachings of which related to those surfactants are incorporated herein by reference.

The following examples merely illustrate the invention. Those skilled in the art will recognize many variations that are within the spirit of the invention and scope of the claims.

Feedstock Syntheses

Preparation of Methyl 9-Decenoate ("C10-0") and Methyl 9-Dodecenoate ("C12-0")

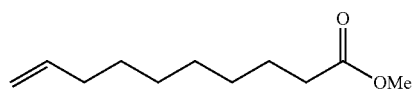

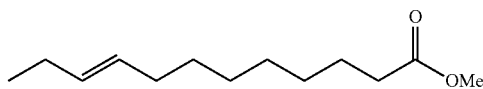

The procedures of U.S. Pat. Appl. Publ. No. 2011/0113679, the teachings of which are incorporated herein by reference, are used to generate feedstocks C10-0 and C12-0 as follows:

Example 1A

Cross-Metathesis of Soybean Oil and 1-Butene

A clean, dry, stainless-steel jacketed 5-gallon Parr reactor equipped with a dip tube, overhead stirrer, internal cooling/heating coils, temperature probe, sampling valve, and relief valve is purged with argon to 15 psig. Soybean oil (SBO, 2.5 kg, 2.9 mol, Costco, $M_n$=864.4 g/mol, 85 weight % unsaturation, sparged with argon in a 5-gal container for 1 h) is added to the Parr reactor. The reactor is sealed, and the SBO is purged with argon for 2 h while cooling to 10° C. After 2 h, the reactor is vented to 10 psig. The dip tube valve is connected to a 1-butene cylinder (Airgas, CP grade, 33 psig headspace pressure, >99 wt. %) and re-pressurized to 15 psig with 1-butene. The reactor is again vented to 10 psig to remove residual argon. The SBO is stirred at 350 rpm and 9-15° C. under 18-28 psig 1-butene until 3 mol 1-butene per SBO olefin bond are transferred into the reactor (~2.2 kg 1-butene over 4-5 h).

A toluene solution of [1,3-bis-(2,4,6-trimethylphenyl)-2-imidazolidinylidene]-dichlororuthenium(3-methyl-2-butenylidene)(tricyclohexylphosphine) (C827, Materia) is prepared in a Fischer-Porter pressure vessel by dissolving 130 mg catalyst in 30 g of toluene (10 mol ppm per mol olefin bond of SBO). The catalyst mixture is added to the reactor via the reactor dip tube by pressurizing the headspace inside the Fischer-Porter vessel with argon to 50-60 psig. The Fischer-Porter vessel and dip tube are rinsed with additional toluene (30 g). The reaction mixture is stirred for 2.0 h at 60° C. and is then allowed to cool to ambient temperature while the gases in the headspace are vented.

After the pressure is released, the reaction mixture is transferred to a round-bottom flask containing bleaching clay (Pure-Flo® B80 CG clay, product of Oil-Dri Corporation of America, 2% w/w SBO, 58 g) and a magnetic stir bar. The reaction mixture is stirred at 85° C. under argon. After 2 h, during which time any remaining 1-butene is allowed to vent, the reaction mixture cools to 40° C. and is filtered through a glass frit. An aliquot of the product mixture is transesterified with 1% w/w NaOMe in methanol at 60° C. By gas chromatography (GC), it contains: methyl 9-decenoate (22 wt. %), methyl 9-dodecenoate (16 wt. %), dimethyl 9-octadecenedioate (3 wt. %), and methyl 9-octadecenoate (3 wt. %).

The results compare favorably with calculated yields for a hypothetical equilibrium mixture: methyl 9-decenoate (23.4 wt. %), methyl 9-dodecenoate (17.9 wt/%), dimethyl 9-octadecenedioate (3.7 wt. %), and methyl 9-octadecenoate (1.8 wt. %).

Example 1B

The procedure of Example 1A is generally followed with 1.73 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (18 wt. %), dimethyl 9-octadecenedioate (2 wt. %), and methyl 9-octadecenoate (2 wt. %).

Example 1C

The procedure of Example 1A is generally followed with 1.75 kg SBO and 3 mol 1-butene/SBO double bond. An aliquot of the product mixture is transesterified with sodium methoxide in methanol as described above. The products (by GC) are: methyl 9-decenoate (24 wt. %), methyl 9-dodecenoate (17 wt. %), dimethyl 9-octadecenedioate (3 wt. %), and methyl 9-octadecenoate (2 wt. %).

Example 1D

The procedure of Example 1A is generally followed with 2.2 kg SBO and 3 mol 1-butene/SBO double bond. Additionally, the toluene used to transfer the catalyst (60 g) is replaced with SBO. An aliquot of the product mixture is transesterified with sodium methoxide in methanol as described above. The products (by GC) are: methyl 9-decenoate (25 wt. %), methyl 9-dodecenoate (18 wt. %), dimethyl 9-octadecenedioate (3 wt. %), and methyl 9-octadecenoate (1 wt. %).

Example 1E

Separation of Olefins from Modified Triglyceride

A 12-L round-bottom flask equipped with a magnetic stir bar, heating mantle, and temperature controller is charged with the combined reaction products from Examples 1A-1D (8.42 kg). A cooling condenser with a vacuum inlet is attached to the middle neck of the flask and a receiving flask is connected to the condenser. Volatile hydrocarbons (olefins) are removed from the reaction product by vacuum distillation. Pot temperature: 22° C.-130° C.; distillation head temperature: 19° C.-70° C.; pressure: 2000-160 µtorr. After removing the volatile hydrocarbons, 5.34 kg of non-volatile residue remains. An aliquot of the non-volatile product mixture is transesterified with sodium methoxide in methanol as described above. The products (by GC) are: methyl 9-decenoate (32 wt. %), methyl 9-dodecenoate (23 wt. %), dimethyl 9-octadecenedioate (4 wt. %), and methyl 9-octadecenoate (5 wt. %). This mixture is also called "UTG-0." (An analogous product made from palm oil is called "PUTG-0.")

Example 1F

Methanolysis of Modified Triglyceride

A 12-L round-bottom flask fitted with a magnetic stir bar, condenser, heating mantle, temperature probe, and gas adapter is charged with sodium methoxide in methanol (1% w/w, 4.0 L) and the non-volatile product mixture produced in Example 1E (5.34 kg). The resulting light-yellow heterogeneous mixture is stirred at 60° C. After 1 h, the mixture turns homogeneous and has an orange color (pH=11). After 2 h of reaction, the mixture is cooled to ambient temperature and two layers form. The organic phase is washed with aqueous methanol (50% v/v, 2×3 L), separated, and neutralized by washing with glacial acetic acid in methanol (1 mol HOAc/mol NaOMe) to pH=6.5. Yield: 5.03 kg.

Example 1G

Isolation of Methyl Ester Feedstocks

A 12-L round-bottom flask fitted with a magnetic stirrer, packed column, and temperature controller is charged with the methyl ester mixture produced in example 1F (5.03 kg), and the flask is placed in a heating mantle. The glass column is 2"×36" and contains 0.16" Pro-Pak™ stainless-steel saddles (Cannon Instrument Co.). The column is attached to a fractional distillation head to which a 1-L pre-weighed flask is fitted for collecting fractions. Distillation is performed under vacuum (100-120 µtorr). A reflux ratio of 1:3 is used to isolate methyl 9-decenoate ("C10-0") and methyl 9-dodecenoate ("C12-0"). Samples collected during the distillation, distillation conditions, and the composition of the fractions (by GC) are shown in Table 1. A reflux ratio of 1:3 refers to 1 drop collected for every 3 drops sent back to the distillation column. Combining appropriate fractions yields methyl 9-decenoate (1.46 kg, 99.7% pure) and methyl 9-dodecenoate (0.55 kg, >98% pure).

TABLE 1

Isolation of C10-0 and C12-0 by Distillation

| Distillation Fractions # | Head temp. (° C.) | Pot temp. (° C.) | Vacuum (µtorr) | Weight (g) | C10-0 (wt %) | C12-0 (wt %) |
|---|---|---|---|---|---|---|
| 1 | 40-47 | 104-106 | 110 | 6.8 | 80 | 0 |
| 2 | 45-46 | 106 | 110 | 32.4 | 99 | 0 |
| 3 | 47-48 | 105-110 | 120 | 223.6 | 99 | 0 |
| 4 | 49-50 | 110-112 | 120 | 283 | 99 | 0 |
| 5 | 50 | 106 | 110 | 555 | 99 | 0 |
| 6 | 50 | 108 | 110 | 264 | 99 | 0 |
| 7 | 50 | 112 | 110 | 171 | 99 | 0 |
| 8 | 51 | 114 | 110 | 76 | 97 | 1 |
| 9 | 65-70 | 126-128 | 110 | 87 | 47 | 23 |
| 10 | 74 | 130-131 | 110 | 64 | 0 | 75 |
| 11 | 75 | 133 | 110 | 52.3 | 0 | 74 |
| 12 | 76 | 135-136 | 110 | 38 | 0 | 79 |
| 13 | 76 | 136-138 | 100 | 52.4 | 0 | 90 |
| 14 | 76 | 138-139 | 100 | 25.5 | 0 | 85 |
| 15 | 76-77 | 140 | 110 | 123 | 0 | 98 |
| 16 | 78 | 140 | 100 | 426 | 0 | 100 |

Preparation of Methyl 9-Hexadecenoate ("C16-0") Feedstock

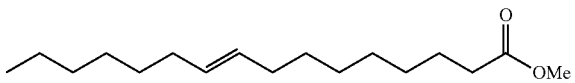 [SMILES: CCCCCC/C=C/CCCCCCCC(=O)OC]

The procedures of Example 1A is generally followed except that 1-octene is cross-metathesized with soybean oil instead of 1-butene. Combined reaction products are then stripped as described in Example 1E to remove the more volatile unsaturated hydrocarbon fraction from the modified oil fraction. The procedure of Example 1F is used to convert the modified oil fraction to a methyl ester mixture that includes methyl 9-hexadecenoate. Fractional distillation at reduced pressure is used to isolate the desired product, methyl 9-hexadecenoate from other methyl esters.

Esteramine Synthesis: General Procedure B

A tertiary alkanolamine (e.g. triethanolamine, N-methyldiethanolamine, N,N-dimethylethanolamine) or an alkoxylated derivative thereof is combined in the same reaction vessel with an ester derivative of 9-decylenic acid, 9-dodecylenic acid, or 9-octadecene-1,18-dioic acid and potassium carbonate. This mixture is heated with agitation at a temperature within the range of 150° C. to 200° C. The relative amounts of amine and ester (or acid) are balanced to provide the desired stoichiometry taking into account the ester/acid content determined by saponification number. The reaction is performed under nitrogen sparge or under vacuum to remove liberated alcohol. When glyceride esters of decylenic acid or dodecylenic acid are used, the liberated glycerin is not removed. The reaction is deemed complete when the desired residual amount of starting amine remains.

Quaternization: General Procedure C

Tertiary amines are converted to methyl quats, betaines, or sulfobetaines by reaction with a quaternizing agent. The quaternization is performed at temperature within the range of 65° C. to 100° C. The quaternizing agent used is dimethyl sulfate for methyl quats, sodium monochloroacetate for betaines, or epichlorohydrin for sulfobetaines. The amount of quaternizing agent used is from 0.8 to 1.0 molar equivalents based on the amount of tertiary amine. The reaction is deemed complete when the free amine value is in the desired range as determined by perchloric acid titration.

Amine Oxides from Amines: General Procedure D

A tertiary amine is diluted with water to form a 10-40 wt. % mixture, which is warmed to 50° C. to 75° C. under nitrogen. Hydrogen peroxide solution (35% solution, 1 to 2.2 molar eq.) is added dropwise while keeping the temperature below 75° C. The mixture is held at the reaction temperature for 4 to 12 h or until the free peroxide level is below 0.2% as determined by starch iodide paper.

Amide Synthesis (Including Amidoamines): General Procedure E

Unsaturated methyl ester ($C_{10}$, $C_{12}$, or $C_{16}$ monoester or $C_{18}$ diester) is combined with 1-6 molar equivalents of a primary or secondary amine (e.g., DMA, DEA, MEA, DMAPA). A base catalyst (e.g., NaOMe or other alkoxide) is added if desired. The reaction mixture is heated at a temperature within the range of 50° C. to 150° C. until the starting ester is substantially consumed. The amide product is purified by distillation, water washing, or other normal means. Alternatively, the product is used "as is" and converted to other derivatives.

Amines by Amide Reduction: General Procedure G

Lithium aluminum hydride (or a similar reducing agent) is dissolved in a solvent (e.g., diethyl ether, THF, dioxane, diglyme) under a nitrogen blanket. A suitable fatty amide is dissolved in the same solvent and is added dropwise, keeping the reaction temperature within the range of 25° C. to 50° C. After the addition, the mixture is stirred overnight at room temperature. Water is carefully added to quench the reaction, and aqueous sodium hydroxide is added. The solids are filtered off, and the solvent is removed. The amine product is purified by distillation.

Imidazoline Synthesis: General Procedure H

Methyl 9-decenoate or methyl 9-dodecenoate is combined with diethylenetriamine (DETA) or 2-(2-aminoethylamino) ethanol (AEEA), with or without a catalyst, in the desired molar ratio of ester groups to primary amino and/or hydroxyl groups. Usually, two moles of ester are used for each mole of DETA or AEEA. The mixture is heated with agitation to a temperature within the range of 140° C. and 200° C. under a mild vacuum that prevents or minimizes evaporation of DETA or AEEA from the reaction mixture. The reaction proceeds until analysis (IR or $^1$H NMR spectroscopy) indicates reasonably complete conversion. The contents are then heated at a temperature within the range of 175° C. to 300° C. with a lower vacuum (5-100 mm Hg) to effect ring closure to the imidazoline. Reaction end point is determined by titration.

Sulfitation of Olefins: General Procedure J

A sulfitating agent (sodium sulfite, sodium bisulfite, sodium metabisulfite, or the like) is dissolved in water and combined with at least a molar equivalent of an olefin. Optionally, a catalyst (peroxides, iron, or other free-radical initiators) is included. The mixture is heated to 50° C.-100° C. for 3-15 h until sulfitation is reasonably complete.

Estolide Preparation: General Procedure K

The procedure used to convert methyl ester C10-0 to its respective fatty acid C10-36 is generally followed as described below.

Sulfonation is carried out in a batch reactor maintained at 20° C. under a nitrogen flow (2 L/min.). The unsaturated fatty acid or an unsaturated fatty acid and saturated fatty acid mixture is added to methylene chloride. Sulfur trioxide is evaporated over 30 min. via a 140° C. flash-pot and is bubbled through the reactor using the nitrogen stream at a molar ratio of $SO_3$ to alkene functionality of about 1:1. The addition rate of $SO_3$ is adjusted to keep the reaction temperature at or below 35° C. At the end of the addition, the reaction mixture is maintained for an additional 5 min. and the mixture is then concentrated under vacuum. The acid product is digested for 1-2 h at 50-85° C. Neutralization is performed using an appropriate base and hydrolysis occurs at 85° C. with the pH maintained with additional base. $^1$H NMR is used to determine complete hydrolysis.

Table 2 summarizes the general procedures used to prepare the following compositions:

TABLE 2

General Methods Used to Synthesize Compositions

| Composition | Methods |
|---|---|
| C10-7 | B, C |
| C10-13 | H, C |
| C10-17* | E |
| C10-18 | E, C |
| C10-20* | E, D |
| C10-21 | E, D, J |
| C10-22 | E, C |
| C10-24 | E, C |
| C10-31 | E, C |
| C10-32* | K |
| C10-39 | E, G, D |
| C10-41 | E, G, C |
| C10-42 | E, G, C |
| C12-7 | B, C |
| C12-16 | H, C |
| C12-17* | E |
| C12-18 | E, C |
| C12-20* | E, D |
| C12-22 | E, C |
| C12-28* | E, G, D |
| C12-40 | E, G, C |
| C12-45 | E, G, C |
| C16-9 | E |
| C16-10 | E, C |
| C16-13 | E, C |
| C16-16 | E, G, C |
| Mix-16 | B, C |
| C18-26* | E |
| Mix-26 | E |
| C18-27 | E, C |
| Mix-27 | E, C |
| C18-29* | E, D |
| Mix-29* | E, D |

TABLE 2-continued

General Methods Used to Synthesize Compositions

| Composition | Methods |
|---|---|
| C18-31 | E, C |
| Mix-31 | E, C |
| C18-32 | E, C |
| Mix-32 | E, C |
| C18-34 | E, C |
| Mix-34 | E, C |
| C18-35* | E, C, D |
| Mix-35* | E, C, D |
| C18-36* | E, C |
| Mix-36* | E, C |
| C18-37* | E, C, D |
| Mix-37 | E, C, D |
| Mix-38 | E, C |
| Mix-44* | E, C |
| Mix-48* | E, C |
| MTG-7 | B, C |
| MTG-12* | E, D |
| MTG-13* | E, C |
| PMTG-5 | E |
| PMTG-12 | E, D |
| PMTG-13 | E, C |
| UTG-6 | E, C |
| UTG-12 | E, D |
| UTG-13 | E, C |
| PUTG-13 | E, C |

Methods: B: alkanolamine transesterification; C: quaternization to methyl quat, betaine, or sulfobetaine; D: oxidation of amine to amine oxide; E: amide from unsaturated ester and primary or secondary amine; G: amine from amide by reduction; H: imidazoline preparation from unsaturated ester + DETA or AEEA; J: sulfitation of olefins; K: estolide preparation
*A detailed procedure for synthesizing this composition is included hereinbelow.

Each of the following compositions is tested as a surfactant in a highly concentrated aqueous glyphosate formulation. Unless otherwise indicated below, the compositions are prepared using the general methods summarized in Table 2:

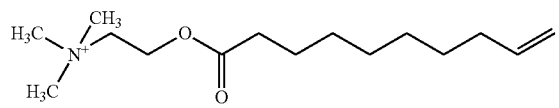

C10-7: C10 DMEA Ester Quat

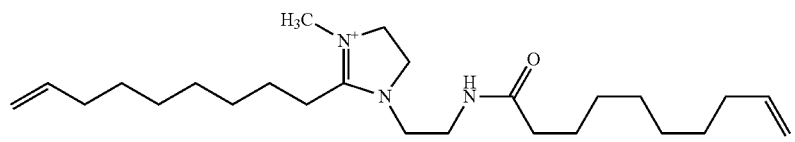

C10-13: C10 DETA Quat

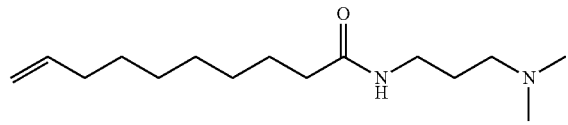

C10-17: C10 DMAPA Amide

A round-bottom flask equipped with nitrogen sparge tube, mechanical stirrer, and Dean-Stark trap is charged with methyl ester C10-0 (500 g, 2.7 mol), 3-(dimethyl-amino) propylamine ("DMAPA," 331 g, 3.24 mol), and sodium methoxide (8.3 g of a 30% solution of in methanol). The reaction mixture is heated to 100° C. and methanol is collected. The reaction temperature is increased in 5° C. increments until the temperature reaches 130° C. The mixture is held at 130° C. for 1 h, and then a sub-surface nitrogen sparge is applied for 2.5 h. The temperature is elevated to 140° C. for an additional 3.5 h. Collected distillate (122 mL) includes methanol and some DMAPA. The reaction mixture is cooled to 110° C., the nitrogen sparge is discontinued, and vacuum was applied. The mixture is stripped of excess DMAPA (150° C., 20 mm Hg, 30 min.). The product, amidoamine C10-17, has an amine value of 224.14 (eq. wt.: 250.28). $^1$H NMR (CDCl$_3$) confirms formation of the amide, based on disappearance of the methyl ester peak at 3.61 ppm and appearance of the DMAPA CH$_2$ signals at 3.27, 2.09, and 1.60 ppm and the N(CH$_3$)$_2$ at 2.18 ppm.

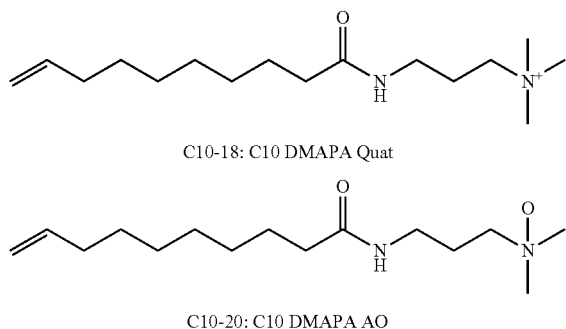

C10-18: C10 DMAPA Quat

C10-20: C10 DMAPA AO

A round-bottom flask is charged with amidoamine C10-17 (162.6 g), water (267 g), and Hamp-Ex 80 (0.5 g). The mixture is heated to 50° C. under nitrogen and several small pieces of dry ice are added. Hydrogen peroxide (35 wt. % aqueous solution, 64.5 g) is added dropwise while keeping the temperature less than 75° C. After completing the H$_2$O$_2$ addition, the mixture is maintained at 70° C. for 7 h. Peroxide paper test indicates <0.5% residual H$_2$O$_2$. The mixture is heated for 3 h at 75° C. and then cooled to room temperature to give amine oxide C10-20 in water. The product comprises (by titration): 35.2% amine oxide; 0.85% free amine.

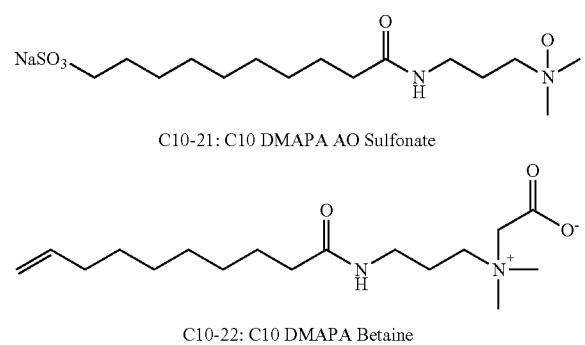

C10-21: C10 DMAPA AO Sulfonate

C10-22: C10 DMAPA Betaine

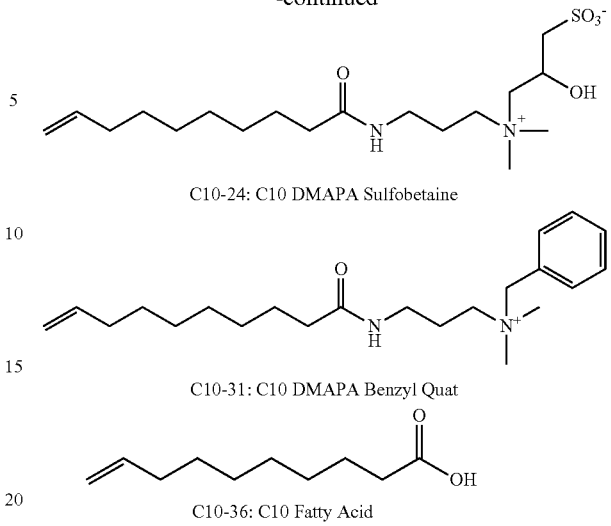

C10-24: C10 DMAPA Sulfobetaine

C10-31: C10 DMAPA Benzyl Quat

C10-36: C10 Fatty Acid

Methyl ester C10-0 (390.2 g) is charged to a round-bottom flask equipped with an overhead stirrer, and the contents are warmed to 70° C. Potassium hydroxide (16% solution in glycerin, 523 g) is added. The mixture is heated to 100° C. and additional KOH pellets (35.10 g) are added. After stirring 17 h, gas chromatography indicates ~94% conversion to the fatty acid. Additional KOH (10 g) is added, and stirring continues at 100° C. for 4 h. Conversion by GC is >97%. The mixture stirs at 100° C. for another 4 h, and is then cooled to 80° C. Water (400 mL) and 30% sulfuric acid solution (500 mL) are added, and the mixture stirs for 1 h. The aqueous phase is then removed. Water (500 mL) is added, and heating/stirring resumes (to 80° C.) for 0.5 h. The aqueous phase is again removed. The water washing process is repeated two more times (2×500 mL). The crude fatty acid product is stripped under vacuum at 80° C. for 2 h to remove water and is used without further purification. Yield: 357 g.

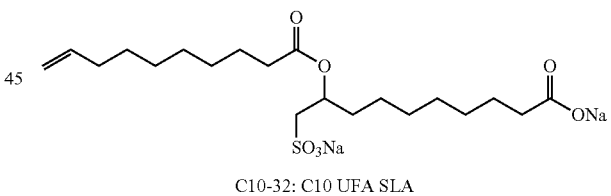

C10-32: C10 UFA SLA

In a sulfonation batch reactor maintained at 20° C. under a nitrogen flow (2 L/min.), C10-36 (109.6 g, 0.64 mol) is added to methylene chloride (100 mL). Sulfur trioxide (51.6 g, 0.64 mol) is evaporated over 30 min. via a 140° C. flash-pot and is bubbled through the reactor using the nitrogen stream. The addition rate of SO$_3$ is adjusted to keep the reaction temperature at or below 35° C. At the end of the addition, the reaction mixture is maintained for an additional 5 min. and the mixture is then concentrated under vacuum. The acid product is then digested for 1 h at 50° C. The acid is neutralized using water (151.0 g) followed by 50% aq. NaOH (41.7 g). Hydrolysis is carried out at 85° C. and pH is maintained with additional 50% aq. NaOH additions. $^1$H NMR analysis supports the proposed composition for sulfo-estolide C10-32. Analytical results: pH: 5.25 (as is); moisture: 51.6 wt. %; sodium sulfate: 0.51 wt. %; unsulfonated matter: 0.79 wt. %.

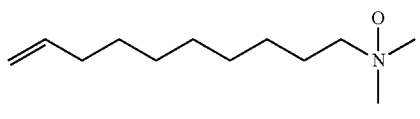

C10-39: C10 Amine Oxide

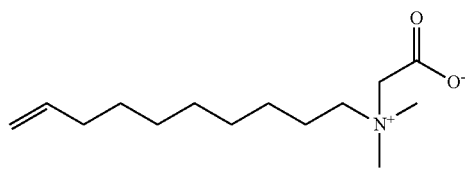

C10-41: C10 Betaine

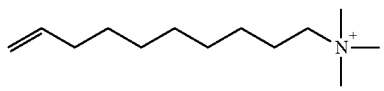

C10-42: C10 AmineDSM Quat

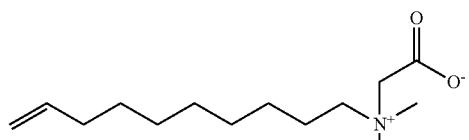

C12-7: C12 DMEA Ester Quat

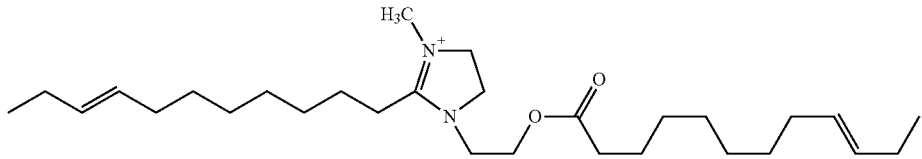

C12-16: AEEA Quat

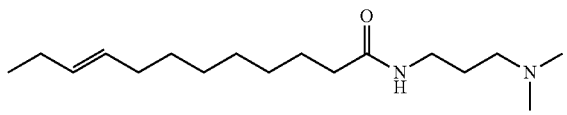

C12-17: C12 DMAPA Amide

The procedure used to make C10-17 is generally followed with methyl ester C12-0 (670 g), DMAPA (387 g), and sodium methoxide (11.2 g of 30 wt. % solution in methanol). The resulting product, amidoamine C12-17, has an amine value of 196.39 (eq. wt.: 281.3). $^1$H NMR (CDCl$_3$) confirms formation of the amide, based on disappearance of the methyl ester peak at 3.61 ppm and appearance of the DMAPA CH$_2$ signals at 3.30, 2.11, and 1.62 ppm and the N(CH$_3$)$_2$ at 2.20 ppm.

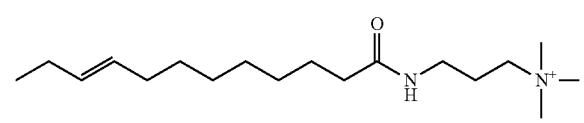

C12-18: C12 DMAPA Quat

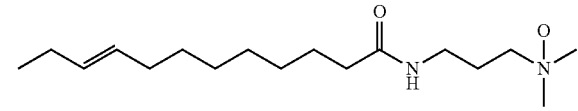

C12-20: C12 DMAPA AO

A round-bottom flask is charged with amidoamine C12-17 (250 g), water (400 g), and Hamp-Ex 80 (0.7 g). Dry ice is added until the pH is 8-9. The mixture is heated to 50° C. under nitrogen. Hydrogen peroxide (35 wt. % solution, 88 g) is added dropwise while maintaining the temperature at less than 75° C. The mixture is maintained at 70° C. for 3 h, then cooled to room temperature overnight. The mixture is reheated to 75° C. and water (50 g) is added to help dissolve solids. The mixture is held at 75° C. for 4 h. Analysis with peroxide test strips indicates trace residual peroxide. The mixture is cooled to recover amine oxide C12-20 as an aqueous solution. The product comprises (by titration): 33.4% amine oxide; 0.06% free amine.

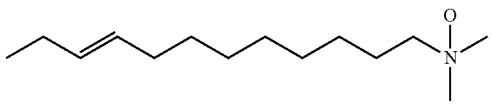

C12-22: C12 DMAPA Betaine

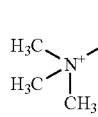

C12-28: C12 Amine Oxide

A round-bottom flask is charged with methyl ester feedstock C12-0 (900.0 g, 4.22 mol) and the material is heated to 60° C. The reactor is sealed and vacuum is applied for 0.5 h to dry/degas the feedstock. The reactor is backfilled with nitrogen, and then sodium methoxide (30 g of 30% solution in methanol) is added via syringe. A static vacuum (−30" Hg) is established, and then dimethylamine (190.3 g, 4.22 mol) is slowly added via sub-surface dip tube. When the pressure equalizes, the reactor is opened to nitrogen overhead and the temperature is increased 70° C. for 1.0 h. The reactor is then cooled to room temperature. Heating resumes to 80° C. and DMA is slowly introduced via sub-surface sparge and held for 2.0 h. The temperature is then increased to 90° C. and held for 1.0 h. $^1$H NMR spectroscopy indicates >98% conversion. The mixture is cooled to 75° C. and full vacuum is applied to strip excess methanol and DMA. The catalyst is quenched by adding 50% aqueous sulfuric acid (16.3 g) and the mixture is stirred vigorously for 10 min. Deionized water (200 mL) is added and all of the contents are transferred to a bottom-draining vessel. The aqueous layer is removed. The wash is repeated with 300 mL and then 150 mL of deionized water. Approximately 50 mL of 20% NaCl solution is added and the mixture settles overnight. The lower layer is removed and the product is transferred back to the reactor. The product is heated to 75° C. and vacuum is applied to remove residual water. The amide, C12-25, is recovered by distillation at 120° C. The amide fraction is placed under full vacuum at 135° C. until the ester content is below 1%. Final ester content: 0.7%. Yield: 875 g (91.9%).

A nitrogen-blanketed 5-L round-bottom flask is charged with tetrahydrofuran ("THF," 1.5 L) and lithium aluminum hydride pellets ("LAH," 67.8 g, 1.79 mol) and is then cooled in an ice bath. Amide C12-25 (620 g, 2.75 mol) is dissolved in THF (250 mL) and charged to an addition funnel. The amide solution is added dropwise over 3 h to the LAH mixture, keeping the reaction temperature below 15° C. The mixture warms to room temperature and stirs for 16 h. The mixture is cooled with an ice bath and deionized water (68 g) is added dropwise to quench residual LAH. Sodium hydroxide (15%, 68 g) and deionized water (204 g) are added, the reaction mixture warms to room temperature. The mixture is filtered, and solvent is stripped from the resulting filtrate. Phthalic anhydride (50 g) is added to convert a by-product fatty alcohol impurity into its corresponding nonvolatile phthalate ester. The desired amine is isolated from the crude mixture by vacuum distillation, collecting overhead liquid at a pot temperature of 115-120° C. Yield of C12-26: 430.7 g (74%). $^1$H NMR (CDCl$_3$) confirms the product as pure amine, based on the integration of the N(CH$_3$)$_2$ peak at 2.18 ppm, the olefinic proton signals at 5.2-5.5 ppm, and the terminal methyl group at 0.93 ppm.

A round-bottom flask equipped with an overhead mechanical stirrer and addition funnel is charged with deionized water (93.5 g) and Hamp-Ex 80 (0.3 g). The mixture is heated to 50° C. while amine C12-26 (137 g, 0.65 mol) and dry ice (−5 g) are added. Hydrogen peroxide (35% solution, 64.3 g, 0.66 mol) is added dropwise to the reaction mixture, allowing the mixture to exotherm to 80° C. and then controlling the reaction at this temperature using a water bath for cooling. The mixture thickens after two-thirds of the H$_2$O$_2$ has been added, and more deonized water (73.7 g) is added. After completing the peroxide addition, the mixture stirs at 80° C. for 24 h until a peroxide test strip indicates low residual peroxide. The ~40% solids reaction mixture is diluted with water to ~37.5% solids to afford a homogenous solution. Titration shows 37.2% C12 amine oxide and 0.009% free amine. Analysis by $^1$H NMR (CDCl$_3$) confirms the formation of the amine oxide, based on shift of the N(CH$_3$)$_2$ peak from 2.18 ppm (for the amine) to 3.12 ppm.

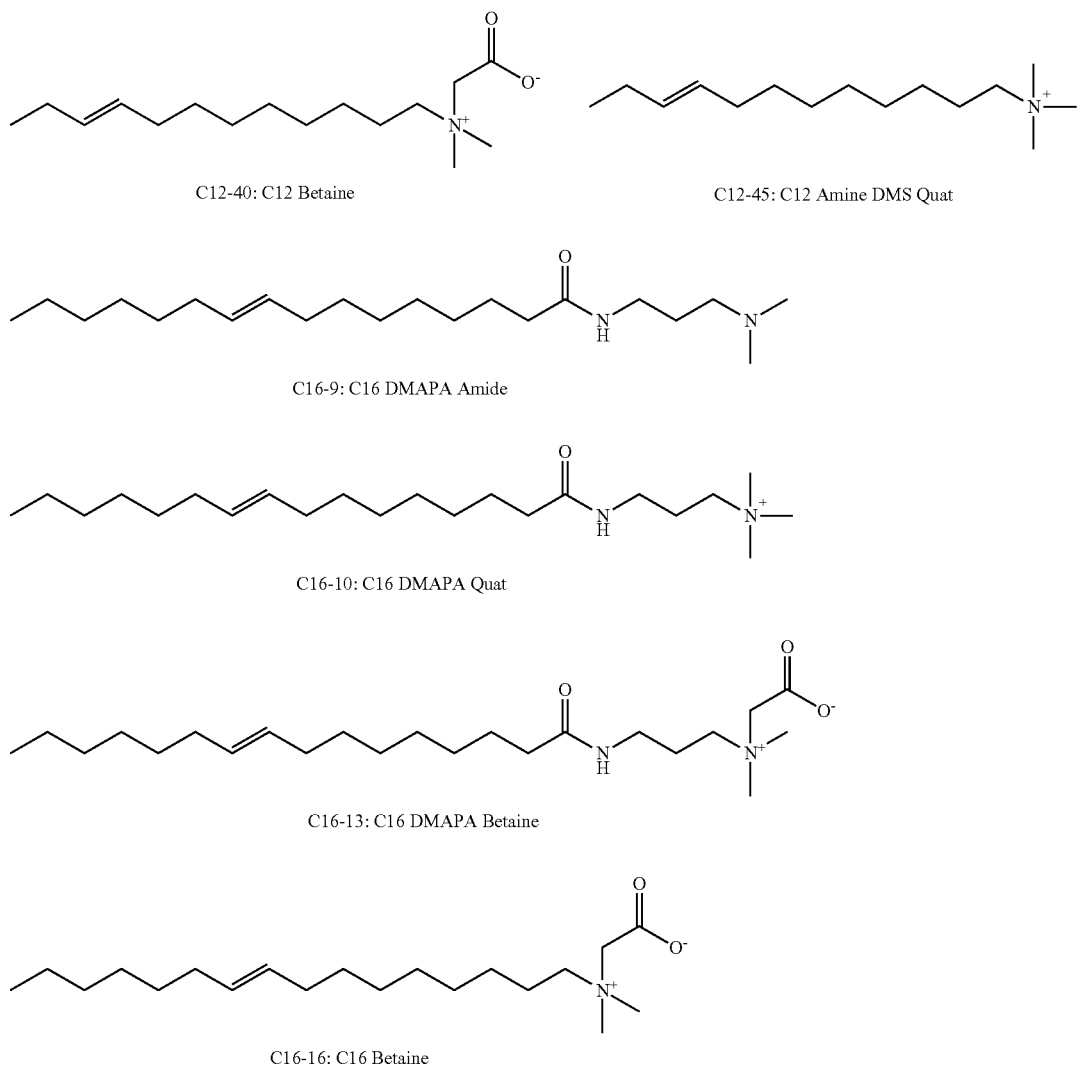

C12-40: C12 Betaine

C12-45: C12 Amine DMS Quat

C16-9: C16 DMAPA Amide

C16-10: C16 DMAPA Quat

C16-13: C16 DMAPA Betaine

C16-16: C16 Betaine

Feedstock Synthesis

Preparation of Dimethyl 9-Octadecene-1,18-dioate ("Mix-0" or "C18-0")

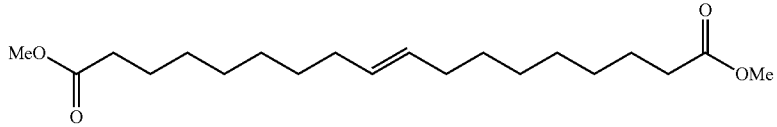 [SMILES: COC(=O)CCCCCCC/C=C/CCCCCCCC(=O)OC]

Eight samples of methyl 9-dodecenoate (10.6 g each, see Table 3) are warmed to 50° C. and degassed with argon for 30 min. A metathesis catalyst ([1,3-bis-(2,4,6-trimethylphenyl)-2-imidazolidinylidene]dichlororuthenium(3-methyl-2-butenylidene)-(tricyclohexylphosphine), product of Materia) is added to the methyl 9-dodecenoate (amount indicated in Table 3) and vacuum is applied to provide a pressure of <1 mm Hg. The reaction mixture is allowed to self-metathesize for the time reported. Analysis by gas chromatography indicates that dimethyl 9-octadecene-1,18-dioate is produced in the yields reported in Table 3. "Mix-0" is an 80:20 trans-/cis-isomer mixture obtained from the reaction mixture. Crystallization provides the all-trans-isomer feed, "C18-0."

TABLE 3

Self-Metathesis of Methyl 9-Dodecanoate

| Sample | Catalyst Loading (ppm mol/mol)* | Reaction Time (h) | C18-0 (GC Area %) |
|---|---|---|---|
| A | 100 | 3 | 83.5 |
| B | 50 | 3 | 82.5 |
| C | 25 | 3 | 83.0 |
| D | 10 | 3 | 66.2 |
| E | 15 | 4 | 90.0 |
| F | 13 | 4 | 89.9 |
| G | 10 | 4 | 81.1 |
| H | 5 | 4 | 50.9 |

*ppm mol catalyst/mol methyl 9-dodecenoate

The tested compounds based on $C_{18}$ feedstock have the following structures:

A round-bottom flask equipped with a mechanical stirrer is charged with diester C18-0 (545.6 g) and DMAPA (343.3 g). A Dean-Stark trap is attached, and sodium methoxide (20 g of 30 wt % solution in MeOH) is added. The temperature is raised to 110° C. over 1.5 h, and methanol is collected. The temperature is increased to 150° C. in increments as the distillation slows. The mixture is held at 150° C. for 6.5 hours and then cooled to room temperature. $^1$H NMR analysis indicates a minor amount of unreacted methyl ester. The mixture is heated to 180° C. for several hours and additional DMAPA and sodium methoxide are added. The mixture is cooled and neutralized with concentrated hydrochloric acid. When the mixture has cooled to 90° C., deionized water is added slowly with vigorous agitation, resulting in precipitation of the amide to afford a slurry. Solids are isolated by vacuum filtration and washed with water. The solid product, all-trans amide C18-26, is dried under vacuum. Yield: 92.2%. $^1$H NMR (CDCl$_3$) confirms formation of the amide, based on disappearance of the methyl ester peak at 3.65 ppm and appearance of the DMAPA CH$_2$ signals at 3.31, 2.12, and 1.62 ppm and the N(CH$_3$)$_2$ at 2.20 ppm.

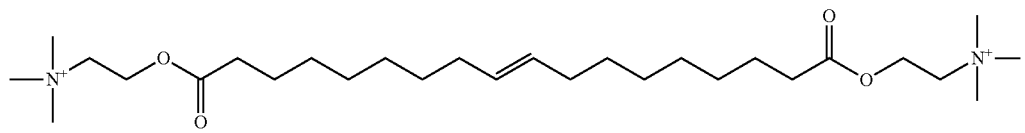

MIX-16: C18 DiDMEA DiQuat (80:20 trans-/cis-)

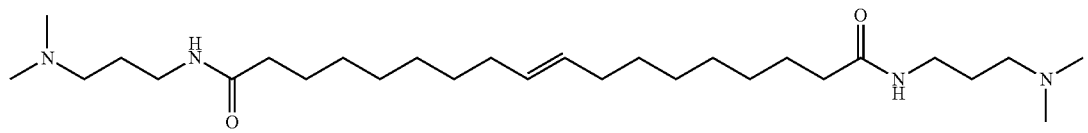

C18-26: C18 DiDMAPA Amide (100% trans-)

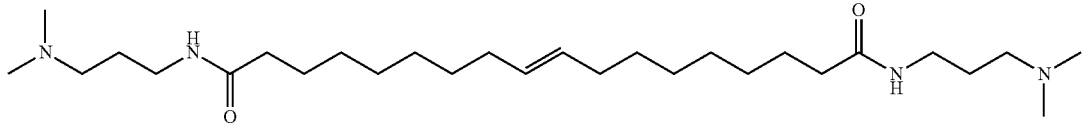

C18 DiDMAPA Amide (80:20 trans-/cis-) MIX-26

C18 DiDMAPA DiQuat (100% trans-) C18-27

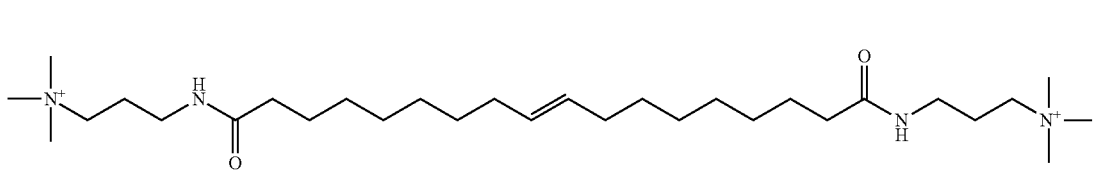

C18 DiDMAPA DiQuat (80:20 trans-/cis-) MIX-27

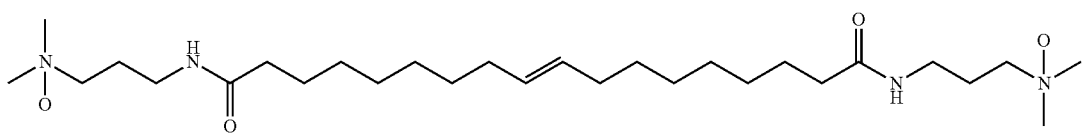

C18 DiDMAPA DiAO (100% trans-) C18-29

A round-bottom flask is charged with amine C18-26 (141.0 g), water (231.2 g), and Hamp-Ex 80 (0.4 g). The mixture is heated to 50° C. and dry ice is added to pH 8.8. When the pH stabilizes, aqueous H₂O₂ (35%, 57.8 g) is added dropwise without heating, keeping the temperature below 75° C. After the peroxide addition is complete, the mixture is warmed at 85° C. for 18 h. The mixture is cooled to room temperature. Titrations reveal: amine oxide: 1.32 meq/g; free amine: 0.027 meq/g; free peroxide: 0.0019%; water: 66.4%.

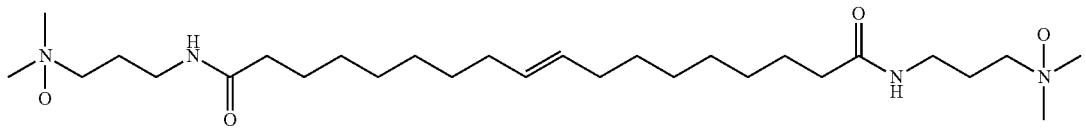

C18 DiDMAPA DiAO (80:20 trans-/cis-) MIX-29

The procedure used to make C18-29 is generally followed with amine Mix-26 (140.0 g), water (230 g), Hamp-Ex 80 (0.4 g), and 35% hydrogen peroxide (57.2 g). Thereafter, titrations indicate: amine oxide: 1.33 meq/g; free amine: 0.046 meq/g; free peroxide: 0.10%; and water: 64.24%.

added dropwise, maintaining temperature below 70° C. After peroxide addition is complete, the mixture is maintained at 70° C. for 20 h. $^1$H NMR indicates complete conversion of tertiary amine to amine oxide. The mixture is cooled to room temperature. Titration shows: amine oxide: 0.50 meq/g; free

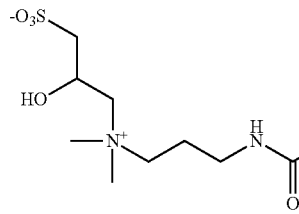
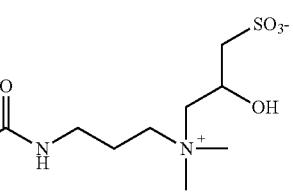

C18-31: C18 DiSulfobetaine (100% trans-)
MIX-31: C18 DiSulfobetaine (80:20 trans-/cis-)

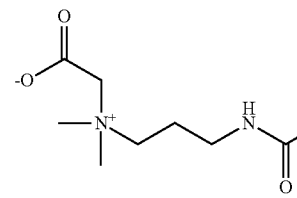
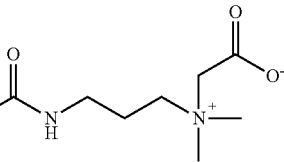

C18-32: C18 DiBetaine (100% trans-)
MIX-32: C18 DiBetaine (80:20 trans-/cis-)

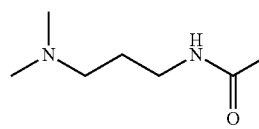
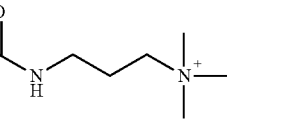

C18-34: C18 DiDMAPA MonoQuat (100% trans-)
MIX-34: C18 DiDMAPA MonoQuat (80:20 trans-/cis-)

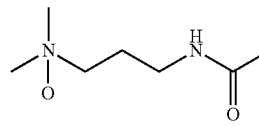
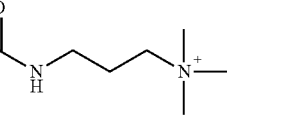

C18-35: C18 DiDMAPA Quat AO (100% trans-)

A round-bottom flask is charged with diamine C18-26 (225.8 g), which is purged with nitrogen and heated to 70° C.

amine: 0.042 meq/g; cationic actives: 0.62 meq/g; free peroxide: 0.08%; and water: 55.8%.

MIX-35

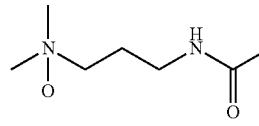

C18 DiDMAPA Quat AO (80:20 trans-/cis-)

Isopropyl alcohol (105.26 g) is added. Dimethyl sulfate (DMS) (58.8 g) is then added slowly via addition funnel so that the temperature is maintained around 70° C. After the DMS addition is complete, the mixture is held at 70° C. for 3 h and then at 85° C. for 1 h to give amine monoquat C18-34.

Amine monoquat C18-34 (75% solids, 192.3 g), deionized water (205.0 g), and Hamp-Ex 80 (0.5 g) are charged to a round-bottom flask. The mixture is heated to 70° C., adjusting pH to >8 with citric acid. Aqueous $H_2O_2$ (35%, 22.86 g) is The procedure used to make C18-34 is generally followed with diamine Mix-26 (241.6 g), isopropyl alcohol (98.4 g), and dimethyl sulfate (60 g). After the DMS addition is complete, the reaction was held at 70° C. for 3 h and then at 85° C. for 3 h. Perchloric acid titration shows 1.317 meq/g of free amine. $^1$H NMR analysis ($CD_3OD$) shows 49% free amine and 51% quaternized amine, based on the integration of the methyl group signals at 2.25 and 3.11 ppm, respectively. The product is Mix-34.

Mix-34 (186.9 g) is dissolved in deionized water (200 g) and stripped of isopropyl alcohol at 75° C. The concentrate (321.6 g) is transferred to a round-bottom flask and Hamp-Ex 80 (0.53 g) is added. The mixture is heated to 50° C. and a few pieces of dry ice are added until the mixture pH is 8-9. Aqueous $H_2O_2$ (35%, 18.23 g) is then added dropwise, maintaining temperature below 70° C. After peroxide addition is complete, the mixture is maintained at 85° C. for 16 h. Deionized water (75 g) is added. The mixture cools to room temperature. $^1H$ NMR analysis is consistent with the proposed structure and shows no detectable free amine. Other analyses show: free peroxide: 0.002%; water: 59.2%.

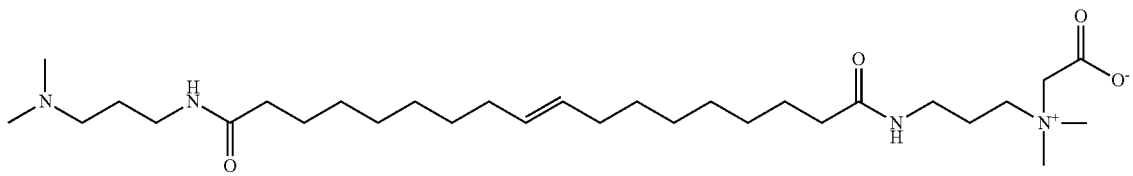

C18 DiDMAPA MonoBetaine (100% trans-)

Amidoamine C18-26 (348 g) and deionized water (500 g) are charged to a round-bottom flask. The mixture is heated to 80° C. and citric acid (2.5 g) is added. A solution made from sodium monochloroacetate (SMCA, 88.5 g) and deionized water (300 g) is added dropwise to the amidoamine solution over 1 h. After the addition is complete, the mixture is heated to 85° C. for 3 h and then 95° C. for 0.5 h. The mixture is then cooled to room temperature. Analysis by silver nitrate titration indicates 3.49% NaCl. Additional SMCA (1.5 g) is added and the mixture is reheated to 95° C. for 6 h. After 6 h, the NaCl content is 3.53%. $^1H$ NMR analysis of a dried aliquot of product shows 45.7% free amine and 54.3% quaternized amine, based on the integration of the methyl group signals at 2.28 and 3.22 ppm, respectively.

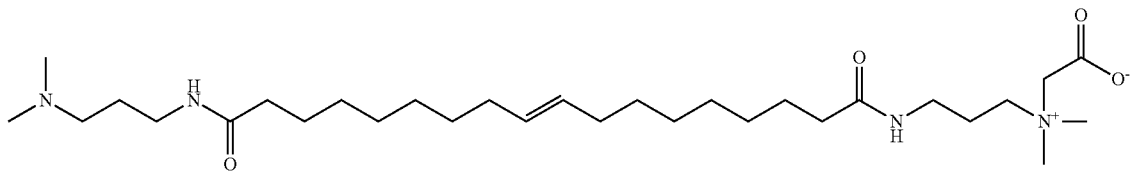

MIX-36: C18 DiDMAPA MonoBetaine (80:20 trans-/cis-)

The procedure used to make C18-36 is generally followed with amidoamine Mix-26 (224.5 g), deionized water (322 g), citric acid (1.5 g), and aqueous sodium monochloroacetate (57 g of SMCA in 200 g of DI water). After the SMCA addition is complete, the mixture is heated to 90° C. for 2 h. Additional SMCA (3.5 g) is added and the mixture is maintained at 90° C. for 2 h. NaCl content: 3.82%. $^1H$ NMR analysis of a dried aliquot shows 44% free amine and 56% quaternized amine.

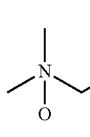

C18-37: C18 DiDMAPA Betaine AO (100% trans-)

Molten monobetaine C18-36 (35% solids, 415.2 g) is charged to a flask and heated to 70° C. Aqueous $H_2O_2$ (35%, 23.6 g) is added dropwise over 0.5 h, maintaining reaction temperature below 78° C. After the peroxide addition is complete, the mixture is stirred at 70° C. for 9 h. $^1$H NMR ($CD_3OD$) of a dried aliquot indicates complete conversion of the monobetaine to the expected amine oxide. Evidence is the disappearance of the $N(CH_3)_2$ peak at 2.28 ppm for the amine and appearance of a peak at 3.15 ppm for the amine oxide $N(CH_3)_2$.

chromatography shows that it contains 94% acid/ester and 6% diacid. Quantitative $^{13}$C NMR shows an 86:14 trans:cis isomer ratio.

MIX-43: C18 Ester/DMAPA Amide (80:20 trans-/cis-)

The mixed acid/ester Mix-69 is converted to the acid chloride/ester by reaction with a slight excess of thionyl chloride ($SOCl_2$) in methylene chloride solution and the product is isolated by removal of the solvent and excess $SOCl_2$ under reduced pressure. $^1$H NMR analysis of the isolated product

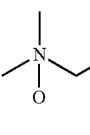

MIX-37: C18 DiDMAPA Betaine AO (80:20 trans-/cis-)

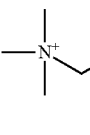

MIX-38: C18 DiDMAPA Betaine Quat (80:20 trans-/cis-)

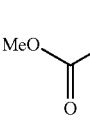

MIX-69: C18 Ester/Acid (80:20 trans-/cis-)

The half-acid/ester Mix-69 is prepared from the dibasic ester Mix-0 (used as received) as described in *Organic Syntheses: Col. Vol. IV* (1963) 635. Thus, Mix-0 (1 kg) is added to methanol (~9 L) and the mixture is stirred mechanically. In a separate vessel, $Ba(OH)_2$ (274.4 g) is dissolved in methanol (~4 L), and the solution is added in portions over 2 h to the stirred diester solution, resulting in the formation of a white precipitate. The solid is isolated by filtration, washed several times with methanol, and dried in air. The solid is then transferred to a 12-L reaction vessel and slurried in ethyl acetate (~3.5 L). Aqueous HCl (32%, Aldrich, 1248.6 g), is added in portions to the stirred slurry, resulting in dissolution of the solid and formation of a clear solution. The solution is washed three times with water, and the aqueous layers are removed and collected in a separate vessel. The combined aqueous layers are extracted once with ethyl acetate, and the organic phase is combined with the washed product solution. The mixture is dried ($Na_2SO_4$), filtered, and concentrated via rotary evaporator. Thorough drying under high vacuum gives a waxy, crystalline solid upon cooling (655 g, ~70% yield). Analysis of the product (following derivatization) by gas shows essentially quantitative conversion to the acid chloride/ester, and the material is used without further purification.

A 3-L reaction vessel equipped with mechanical stirrer, nitrogen inlet, and thermocouple is charged with methylene chloride (200 mL), DMAPA (172.1 g), and pyridine (133.3 g). The previously prepared acid chloride/ester is added dropwise to the stirred DMAPA-pyridine solution. During the addition, the temperature is maintained at 25-40° C. by cooling with an ice bath as required, and the addition is completed in 1.5 h. A precipitate forms, and after stirring overnight at room temperature, the mixture has become a thick slurry. The mixture is diluted with methylene chloride (500 mL), and water (500 mL) is added, giving a clear homogeneous solution. Addition of ethyl acetate fails to induce phase separation. However, addition of saturated NaCl solution causes slow separation of a lower aqueous phase, which is drained and discarded. Concentration of the organic phase via rotary evaporation gives a viscous brown oil. $^1$H NMR analysis shows free pyridine and indicates that the terminal tertiary amine of the DMAPA moiety is protonated. The material is taken up in acetone and the mixture is filtered to remove a small quantity of precipitated solid. The pH of the solution is adjusted to ~8.5 (measured on as-is material) with 50% aq. NaOH, resulting in the formation of a solid precipitate. The mixture is filtered again and the clear filtrate is concentrated and then dried under high vacuum. On cooling, the material solidifies. $^1$H NMR analysis is consistent with the target structure and shows the presence of free pyridine. The product is heated to 60° C., stirred, and sparged with sub-surface nitrogen under reduced pressure for 5 h, then at 105° C. for 30 min. After stripping, $^1$H NMR analysis of the product showed no residual pyridine.

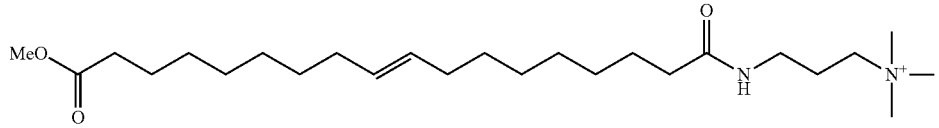

MIX-44: C18 Ester DMAPA Quat (80:20 trans-/cis-)

Ester-amidoamine Mix-43 (162.7 g) is charged to a flask equipped with mechanical stirring, thermocouple, and nitrogen inlet. Isopropanol (IPA; 47.8 g) is added, and the mixture is heated to 70° C. Perchloric acid titration of the ester/amide starting material is used to calculate the required amount of dimethylsulfate (DMS). The DMS (28.6 g) is added dropwise while maintaining the reaction temperature at 70° C. with external cooling. After the DMS addition is complete, the mixture is stirred at 70° C. for 3 h, then for 1 h at 85° C. Perchloric acid titration shows nearly complete consumption of the tertiary amine. The quat product, Mix-44, cools to give a waxy solid. Analysis for residual DMS via Drager apparatus is negative.

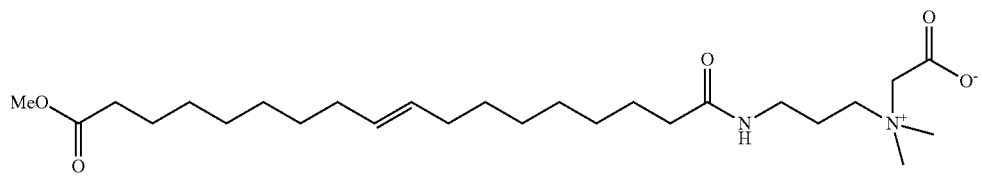

MIX-48: C18 Ester DMAPA Betaine (80:20 trans-/cis-)

A round-bottom flask fitted with a thermocouple, nitrogen inlet, and mechanical stirring is charged with ester-amidoamine Mix-43 (134.2 g, 0.327 mol). Water (250 mL) and sodium monochloroacetate (38.9 g, 0.334 mol) are added. The mixture is warmed to 70° C. and after approximately 1 h, it becomes clear. During the reaction, the pH of the mixture is maintained at ~8 with 50% aq. NaOH. Heating continues for 5 h at 70° C. The $^1$H NMR spectrum is consistent with the proposed structure and shows no residual tertiary amine. The product, ester-betaine Mix-48, is cooled and analyzed: water: 59.9%; NaCl: 4.29%.

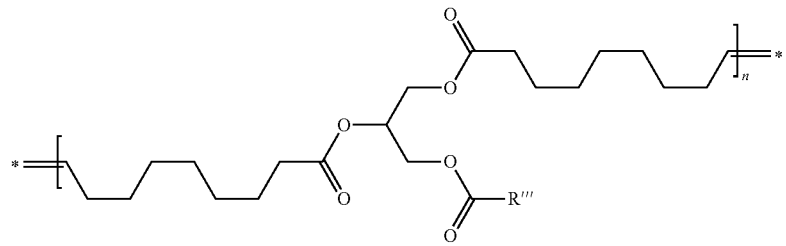

Modified Triglyceride Based on Soybean Oil ("MTG-0")

The procedures of Examples 1A and 1E are generally followed except that 1-butene is omitted.

The procedure used to make MTG-0 is followed, except that palm oil is used instead of soybean oil.

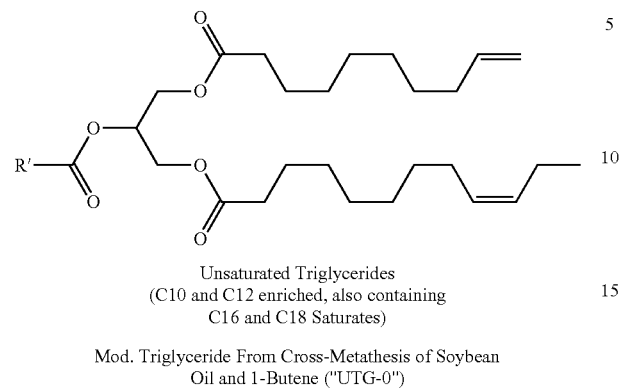

Unsaturated Triglycerides
(C10 and C12 enriched, also containing C16 and C18 Saturates)

Mod. Triglyceride From Cross-Metathesis of Soybean Oil and 1-Butene ("UTG-0")

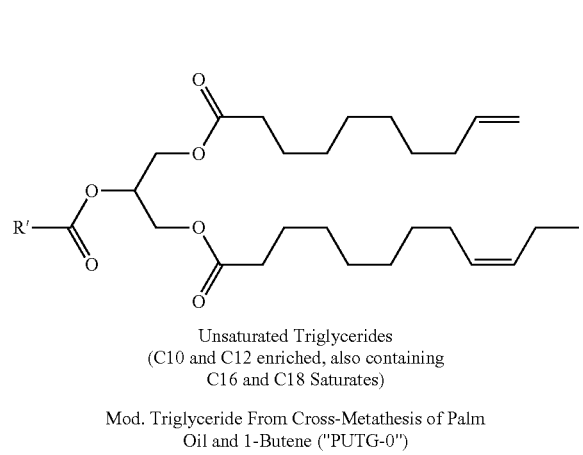

Unsaturated Triglycerides
(C10 and C12 enriched, also containing C16 and C18 Saturates)

Mod. Triglyceride From Cross-Metathesis of Palm Oil and 1-Butene ("PUTG-0")

The procedures of Examples 1A and 1E are generally followed to produce UTG-0 from soybean oil and 1-butene.

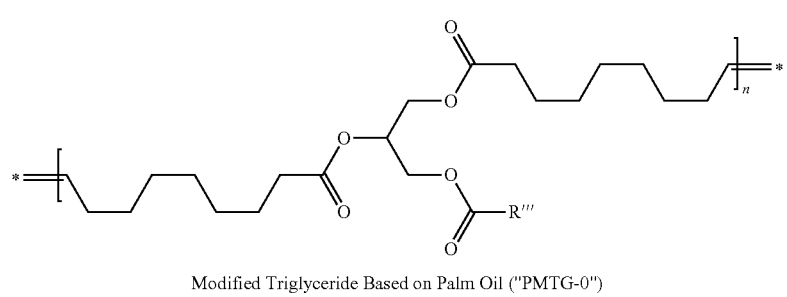

Modified Triglyceride Based on Palm Oil ("PMTG-0")

The procedure used to make UTG-0 is followed, except that palm oil is used instead of soybean oil.

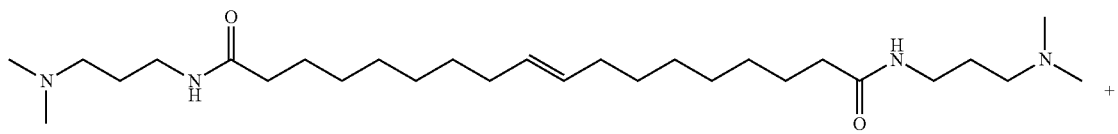

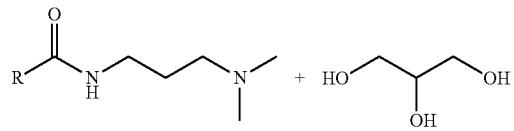

MTG-0 Feedstock Derivatives
MTG-5: MTG DMAPA Amide Mix

R = C16, C18 Sat. + Unsat.

A round-bottom flask is charged with MTG-0 (180 g, saponification value=226.5 mg KOH/g, 0.73 mol), and the contents are heated to 50° C. The mixture is purged with nitrogen for 1 h and dimethylaminopropylamine (DMAPA, 78 g, 0.76 mol) and NaBH₄ (0.1 g) are added. The mixture is heated to 160° C. for 18 h. Excess amine is removed by short-path distillation (135° C., 30 mm Hg), and the product is cooled to room temperature to afford amidoamine mixture MTG-5. Amine value: 172.9 mg KOH/g (eq. wt.: 324.45 g/mol). Free DMAPA: 1.80%; iodine value: 71.9 g I₂/100 g sample.

with stirring. Dry ice is added in small pieces resulting in a homogeneous solution. Thereafter, 35% H₂O₂ (43.4 g, 0.47 mol) is added over 15 min., and the reaction temperature increases to 69° C. The initially viscous solution becomes thinner as more peroxide is added. When peroxide addition is complete, the mixture is cooled to 65° C. and allowed to stir for 4 h. Free peroxide: <2 mg/L. The reaction mixture cools to room temperature and stands overnight under a nitrogen purge. The product mixture shows no measurable peroxide. Additional 35% H₂O₂ solution (2.15 g) is added, and the

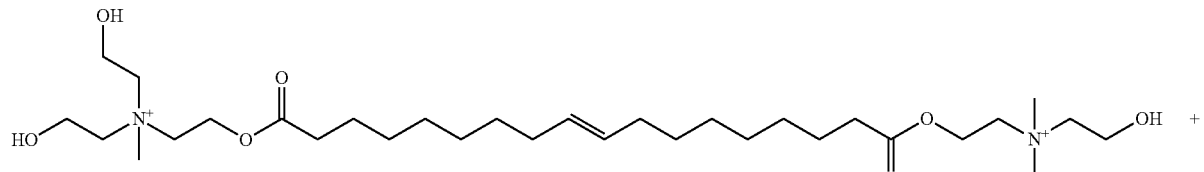

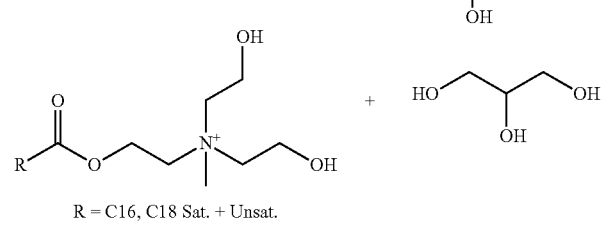

R = C16, C18 Sat. + Unsat.

MTG-7: MTG TEA Ester (1:1) Quat

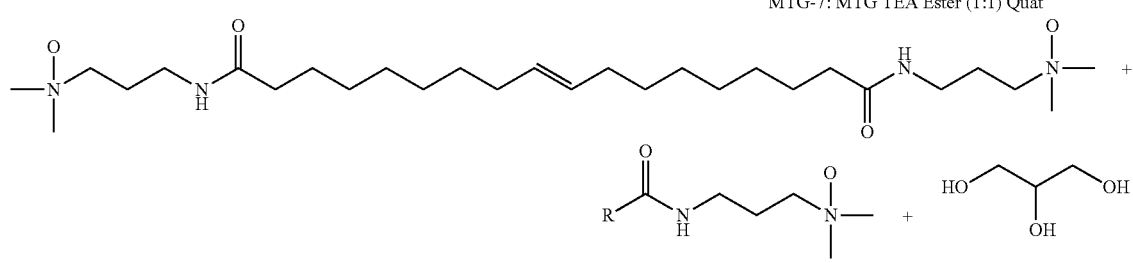

R = C16, C18 Sat. + Unsat.

MTG-12: MTG DMAPA AO

Molten MTG-5 (145.5 g, 0.42 mol) and deionized water (303.7 g) are charged to a reaction flask equipped with reflux condenser, addition funnel, thermocouple, mechanical stirrer, and nitrogen inlet. The reactor contents are heated to 40° C.

mixture is heated to 65° C. for 4 h. Upon cooling, analysis of the MTG-12 product shows: pH (10% aqueous): 7.44; water: 69.5%; free amine: 1.52%; amine oxide actives: 29.1%; hydrogen peroxide: 0.01%.

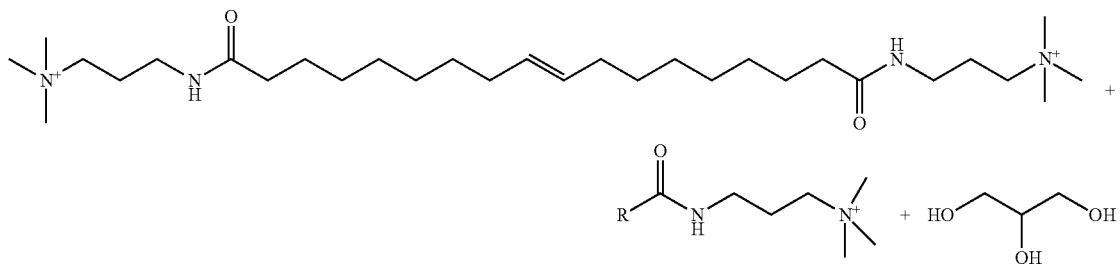

MTG-13: MTG DMAPA DMS Quat

R = C16, C18 Sat. + Unsat.

A nitrogen-purged flask is charged with MTG-5 (159.9 g) and the contents are warmed to 80° C. Dimethyl sulfate (56.86 g) is added. The mixture is warmed to 95° C., but viscosity remains high, so temperature is reduced to 70° C. and isopropyl alcohol (25.5 g) is added. The reaction stirs for 3 h at 70° C. and is allowed to cool. Analysis of the quat product, MTG-13, shows: free amine: 0.055 meq/g; moisture: 0.13 wt. %; active quat: 1.80 meq/g.

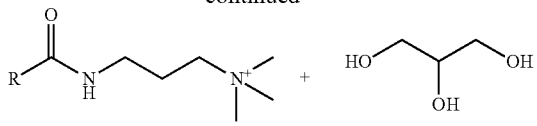

R = C16, C18 Sat.

PUTG-13: PUTG DMAPA DMS Quat

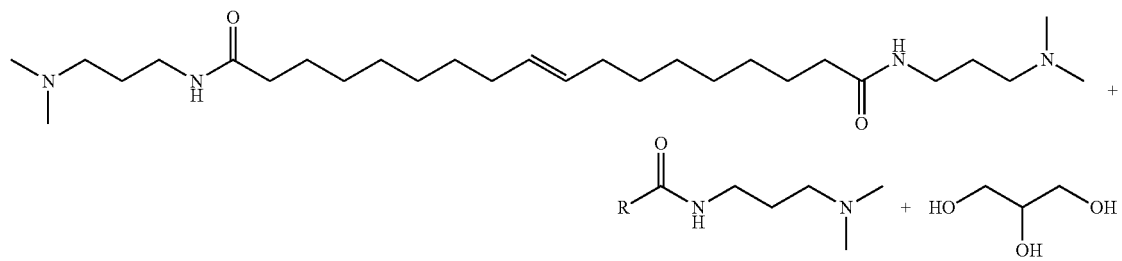

R = C16, C18 Sat. + Unsat.

PMTG-5: PMTG DMAPA Amide Mix

Analogous procedures are used to make the corresponding products starting from PMTG-0, UTG-0, and PUTG-0. The products from modified triglycerides are summarized below in Table 4.

The other PMTG products (PMTG-12 and PMTG-13) have analogous structures to the MTG products. The UTG and PUTG products have structures as shown below.

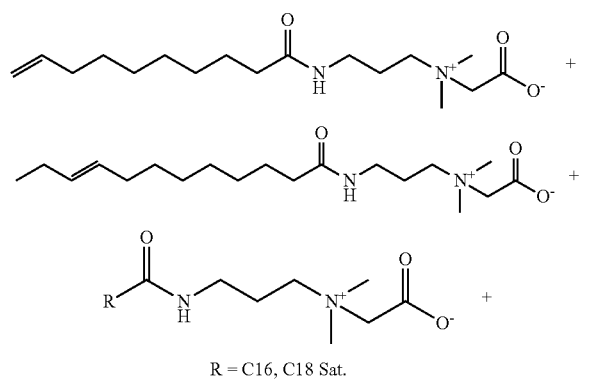

UTG-6: UTG DMAPA Betaine Mix

TABLE 4

Summary of Modified Triglyceride Products

| | Soybean Oil | | Palm Oil | |
|---|---|---|---|---|
| | Self-met. MTG-0 | X-met. UTG-0 | Self-met. PMTG-0 | X-met. PUTG-0 |
| DMAPA Amide Mix | MTG-5 | | PMTG-5 | |
| DMAPA Betaine Mix | | UTG-6 | | |
| TEA Ester (1:1) Quat | MTG-7 | | | |
| DMAPA AO | MTG-12 | UTG-12 | PMTG-12 | |
| DMAPA DMS Quat | MTG-13 | UTG-13 | PMTG-13 | PUTG-13 |

Agricultural Glyphosate Formulations: Formulation Stability
Sample Preparation:

A 44.0% acid equivalent (a.e.) formulation is prepared by first charging glyphosate acid (486.19 g, 90.5% a.e., product of Monsanto) to an ice-cooled 1-L reaction vessel equipped with a mixer and temperature probe. Deionized water (337.23 g) is added with mixing to generate a glyphosate acid slurry. Potassium hydroxide pellets (176.58 g, 86.6% KOH, Fisher) are slowly added such that the temperature of the solution does not exceed 50° C. The mixture is then allowed to cool to room temperature and is mixed until a clear glyphosate concentrate of 44% a.e. results. The pH of the concentrate is measured by preparing a 10% solution of the concentrate in deionized water and measuring it with a pH electrode. If the pH of the concentrate is between 4.2 and 4.4 the concentrate is used as is. If the pH needs to be adjusted, then glyphosate acid, KOH, and water are added in appropriate quantities to yield the correct pH while maintaining the 44% a.e. level of the concentrate required.

Stability Testing:

A test surfactant (5.0 g) is added to 45.0 g of the glyphosate concentrate above (44% a.e.) to yield a glyphosate formulation concentrate, ~39.6% a.e. (~540 g/L a.e. K salt). This concentrate is mixed until a clear solution results. If no clear solution results, an aliquot of lauryl dimethyl amine oxide (LDMAO) (~55-60% actives, product of Stepan) is added to the surfactant to make a 90:10 surfactant:LDMAO blend.

This is then tested for stability as above. If that does not pass, the procedure of adding LDMAO to the surfactant continues until a ratio is found that gives a stable glyphosate formulation. If no stable formulation can be made, the surfactant is deemed incompatible with glyphosate. If a clear homogeneous solution results, the sample is split in two and placed both in a 54° C. oven and a −10° C. freezer for two weeks. If there is no haziness or separation, the formulation is considered stable at that temperature.

The control surfactant is a $C_{12}$-$C_{14}$ DMEA esterquat. This is prepared by reacting a mixture of lauric ($C_{12}$) and myristic ($C_{14}$) acids with N,N-dimethylethanolamine (DMEA) at 140° C. for 5 h, then heating to 175° C. to complete the reaction. Quaternization with methyl chloride in propylene glycol at 80° C. at 40 psig in the usual way provides the desired esterquat. The control surfactant gives a clear formulation at room temperature but the formulation separates at −10° C. Addition of amine oxide in a 9:1 to 1:1 ratio (control surfactant to amine oxide) is needed to give a desirable stability with the control.

As shown in Tables 5A and 5B, eighteen samples outperform the control, and twenty-two samples perform as well as the control, while eighteen samples show inferior performance in the stability testing.

The results demonstrate that it is not easy to predict which classes of compounds will provide superior performance when glyphosate formulation stability is evaluated at room temperature, 54° C. and −10° C. For instance, C10-17, a $C_{10}$ DMAPA amide earns a superior rating, but C12-17, the $C_{12}$ analog performs equal to the control in the test. In another example, the $C_{10}$ and $C_{12}$ betaines (C10-41 and C12-40) perform equal to the control, but the $C_{10}$ and $C_{12}$ DMAPA betaines (C10-22 and C12-22) are inferior in the test.

As further evidence of unpredictability, we sometimes noted advantages of selecting 100% trans-$C_{18}$ compositions when compared with their very similar 80:20 trans-/cis-analogs (see Tables 5A and 5B, C18-26 versus Mix-26). However, other 80:20 trans-/cis-compositions performed as well as their all-trans counterparts (see C18-29 versus Mix-29 or C18-35 versus Mix-35).

TABLE 5A

Glyphosate Formulation Stability: 540 g.a.e./L K salts
Inventive Examples

| Sample | AO added | RT | Stable at: −10° C. | 54° C. | Comment | Rating |
|---|---|---|---|---|---|---|
| C10-17 | N | Y | Y | Y | low viscosity at −10° C. | superior |
| C10-20 | N | Y | Y | Y | | superior |
| C12-20 | N | Y | Y | Y | low viscosity at −10° C. | superior |
| C12-28 | N | Y | Y | Y | | superior |
| C18-26 | N | Y | Y | Y | good results at 5% sample | superior |
| C18-29 | N | Y | Y | Y | | superior |
| Mix-29 | N | Y | Y | Y | | superior |
| C18-35 | N | Y | Y | Y | | superior |
| Mix-35 | N | Y | Y | Y | | superior |
| C18-36 | N | Y | Y | Y | | superior |
| Mix-36 | N | Y | Y | Y | | superior |
| C18-37 | N | Y | Y | Y | | superior |
| Mix-44 | N | Y | Y | Y | 5% sample | superior |
| MTG-12 | N | Y | Y | Y | | superior |
| MTG-13 | Y | Y | Y | Y | 6% sample, 2.5% PG, 1.5% AO | superior |
| PMTG-5 | N | Y | Y | Y | | superior |
| UTG-12 | N | Y | Y | Y | | superior |

TABLE 5A-continued

Glyphosate Formulation Stability: 540 g.a.e./L K salts
Inventive Examples

| Sample | AO added | RT | Stable at: −10° C. | 54° C. | Comment | Rating |
|---|---|---|---|---|---|---|
| UTG-13 | N | Y | Y | Y | 5% sample | superior |
| C10-13 | Y | Y | Y | Y | 5% sample | good |
| C10-18 | Y | Y | Y | Y | 5% sample | good |
| C10-39 | N | Y | Y | Y | comparable to decylamine oxide | good |
| C10-41 | Y | Y | Y | Y | 5% sample | good |
| C10-42 | Y | Y | Y | Y | 5% sample | good |
| C12-17 | Y | Y | Y | Y | 5% sample; + AO for low viscosity | good |
| C12-18 | Y | Y | Y | Y | 6% sample | good |
| C12-40 | Y | Y | Y | Y | 5% sample | good |
| C12-45 | Y | Y | Y | Y | 5% sample | good |
| C16-9 | Y | Y | Y | Y | 5% sample; + AO for low viscosity | good |
| C16-13 | Y | Y | Y | Y | 5% sample + propylene glycol | good |
| C16-16 | Y | Y | Y | Y | 5% sample + propylene glycol | good |
| Mix-26 | Y | Y | Y | Y | | good |
| C18-27 | Y | Y | Y | Y | 5% sample | good |
| Mix-27 | Y | Y | Y | Y | | good |
| C18-34 | N | Y | Y | Y | 6% sample | good |
| Mix-37 | N | Y | Y | Y | 5% sample | good |
| Mix-38 | Y | Y | Y | Y | 5% sample | good |
| PMTG-12 | N | Y | Y | Y | 5% sample; +water for low viscosity | good |
| PMTG-13 | N | Y | Y | Y | 60% sol. in propylene glycol passes | good |
| PUTG-13 | Y | Y | Y | Y | | good |
| UTG-6 | Y | Y | Y | Y | 5% sample | good |

TABLE 5B

Glyphosate Formulation Stability: 540 g.a.e./L K salts
Comparative Examples

| Sample | AO added | RT | Stable at: −10° C. | 54° C. | Comment | Rating |
|---|---|---|---|---|---|---|
| C10-7 | Y | Y | Y | N | | inferior |
| C10-21 | N | N | — | N | | inferior |
| C10-22 | N | N | — | N | | inferior |
| C10-24 | N | N | — | N | | inferior |
| C10-31 | Y | Y | N | Y | | inferior |
| C10-32 | N | N | — | N | | inferior |
| C12-7 | Y | Y | Y | N | | inferior |
| C12-16 | Y | N | — | — | | inferior |
| C12-22 | N | N | — | N | | inferior |
| C16-10 | Y | N | N | N | | inferior |
| Mix-16 | Y | Y | Y | N | | inferior |
| C18-31 | Y | Y | N | Y | | inferior |
| Mix-31 | Y | Y | N | Y | | inferior |
| C18-32 | Y | Y | N | Y | | inferior |
| Mix-32 | Y | Y | N | Y | | inferior |
| Mix-34 | Y | Y | N | Y | | inferior |
| Mix-48 | Y | N | N | N | | inferior |
| MTG-7 | N | N | — | N | | inferior |

The preceding examples are meant only as illustrations. The following claims define the invention.

We claim:

1. A glyphosate formulation comprising a glyphosate salt, water, and a surfactant derived from a metathesis-derived $C_{10}$-$C_{17}$ monounsaturated acid, octadecene-1,18-dioic acid, or their ester derivatives and, wherein the surfactant produced from a $C_{10}$-$C_{17}$ monounsaturated acid, octadecene-1,18-dioic acid or its ester derivative wherein the $C_{10}$-$C_{17}$ monounsaturated acid, octadecene-1,18-dioic acid or their ester derivative is produced by a metathesis reaction, wherein the surfactant is selected from the group consisting of $C_{10}$ or $C_{12}$ amine oxides, $C_{10}$ or $C_{12}$ quats, $C_{10}$, $C_{12}$, or $C_{16}$ amidoamines, $C_{10}$ or $C_{12}$ amidoamine oxides, $C_{10}$ imidazoline quats, $C_{10}$ or $C_{12}$ amidoamine quats, $C_{10}$, $C_{12}$, or $C_{16}$ betaines, $C_{16}$ amidoamine betaines, $C_{18}$ diamidoamines, $C_{18}$ diamidoamine oxides, $C_{18}$ diamidoamine diquats, $C_{18}$ diamidoamine oxide quats, $C_{18}$ diamidoamine oxide betaines, $C_{18}$ diamidoamine monobetaines, $C_{18}$ diamidoamine monobetaine quats, $C_{18}$ ester amidoamine quats; amidoamines and their oxidized or quaternized derivatives made from self-metathesized palm or soybean oil; and amidoamines and their oxidized or quaternized derivatives produced from cross-metathesized palm or soybean oil wherein the formulation remains a clear, homogenous solution after two weeks at $-10°$ C.

2. The formulation of claim 1 wherein the surfactant is selected from the group consisting of $C_{12}$ amine oxides, $C_{10}$ amidoamines, $C_{10}$ or $C_{12}$ amidoamine oxides, $C_{18}$ diamidoamines, $C_{18}$ diamidoamine oxides, $C_{18}$ diamidoamine monobetaines, $C_{18}$ diamidoamine oxide betaines, $C_{18}$ diamidoamine oxide quats, $C_{18}$ ester amidoamine quats; amidoamines and their oxidized or quaternized derivatives made from self-metathesized palm or soybean oil; and amidoamines and their oxidized or quaternized derivatives made from cross-metathesized palm or soybean oil.

3. The formulation of claim 2 wherein the surfactant is selected from the group consisting of $C_{12}$ amine oxides, $C_{10}$ amidoamines, and $C_{10}$ or $C_{12}$ amidoamine oxides.

4. The formulation of claim 2 wherein the surfactant is selected from the group consisting of $C_{18}$ diamidoamines, $C_{18}$ diamidoamine oxides, $C_{18}$ diamidoamine monobetaines, $C_{18}$ diamidoamine oxide betaines, $C_{18}$ diamidoamine oxide quats, and $C_{18}$ ester amidoamine quats.

5. The formulation of claim 2 wherein the surfactant is selected from the group consisting of amidoamines and their oxidized derivatives made from self-metathesized palm or soybean oil; and amidoamines and their oxidized or quaternized derivatives made from cross-metathesized palm or soybean oil.

6. The formulation of claim 1 comprising at least 30 wt. % acid equivalents of the glyphosate salt.

7. The formulation of claim 1 wherein the $C_{10}$-$C_{17}$ monounsaturated acid, octadecene-1,18-dioic acid or its ester derivative has at least 1 mole % of trans-$\Delta^9$ unsaturation.

8. The formulation of claim 1 comprising from 0.1 to 15 wt. % of the surfactant.

9. The formulation of claim 1 further comprising an auxiliary surfactant selected from the group consisting of amine oxides and betaines.

10. The formulation of claim 1 wherein the surfactant is selected from the group consisting of $C_{10}$ amine oxides, $C_{10}$ or $C_{12}$ quats, $C_{12}$ or $C_{16}$ amidoamines, $C_{10}$ imidazoline quats, $C_{10}$ or $C_{12}$ amidoamine quats, $C_{10}$, $C_{12}$, or $C_{16}$ betaines, $C_{16}$ amidoamine betaines, $C_{18}$ diamidoamine diquats, $C_{18}$ diamidoamine monobetaine quats; amidoamines and their oxidized or quaternized derivatives made from self-metathesized palm or soybean oil; and amidoamines and their oxidized or quaternized derivatives made from cross-metathesized palm or soybean oil.

11. The formulation of claim 10 wherein the surfactant is selected from the group consisting of $C_{10}$ amine oxides, $C_{10}$ or $C_{12}$ quats, $C_{12}$ or $C_{16}$ amidoamines, $C_{10}$ imidazoline quats, $C_{10}$ or $C_{12}$ amidoamine quats, $C_{10}$, $C_{12}$, or $C_{16}$ betaines, and $C_{16}$ amidoamine betaines.

12. The formulation of claim 10 wherein the surfactant is selected from the group consisting of $C_{18}$ diamidoamine diquats and $C_{18}$ diamidoamine monobetaine quats.

13. The formulation of claim 10 wherein the surfactant is selected from the group consisting of amidoamines and their oxidized or quaternized derivatives made from self-metathesized palm or soybean oil; and amidoamines and their oxidized or quaternized derivatives made from cross-metathesized palm or soybean oil.

14. The formulation of claim 10 comprising at least 30 wt. % acid equivalents of the glyphosate salt.

15. The formulation of claim 10 comprising from 0.1 to 15 wt. % of the surfactant.

16. The formulation of claim 10 further comprising an auxiliary surfactant selected from the group consisting of amine oxides and betaines.

\* \* \* \* \*